US011351147B2

(12) United States Patent
Crossley et al.

(10) Patent No.: US 11,351,147 B2
(45) Date of Patent: Jun. 7, 2022

(54) SHORT SYNTHESES OF (−)-PICROTOXININ AND RELATED COMPOUNDS

(71) Applicant: The Scripps Research Institute, La Jolla, CA (US)

(72) Inventors: Steven W. M. Crossley, Kensington, CA (US); Guanghu Tong, San Diego, CA (US); Michael Lambrecht, Burlingame, CA (US); Ryan Shenvi, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/947,560

(22) Filed: Aug. 6, 2020

(65) Prior Publication Data

US 2022/0040147 A1 Feb. 10, 2022

(51) Int. Cl.

| | |
|---|---|
| *A61K 31/365* | (2006.01) |
| *C07D 493/18* | (2006.01) |
| *C07D 493/22* | (2006.01) |
| *A61P 25/00* | (2006.01) |
| *A61K 31/366* | (2006.01) |

(52) U.S. Cl.

CPC .......... *A61K 31/365* (2013.01); *A61K 31/366* (2013.01); *A61P 25/00* (2018.01); *C07D 493/18* (2013.01); *C07D 493/22* (2013.01)

(58) Field of Classification Search

CPC .. C07D 493/18; C07D 493/22; A61K 31/365; A61K 31/366

See application file for complete search history.

(56) References Cited

PUBLICATIONS

Crossley et al. J. Am. Chem. Soc. 2020, 142, 11376-11381. (Year: 2020).*

Crossley, Steven W.M., et al., "Synthesis of (−)-Picrotoxinin by Late-Stage Strong Bond Activation", J. Am. Chem. Soc. 2020, 142, 11376-11381, (2020), 11376-11381.

Crossley, Steven W.M., et al., "Total Synthesis of (−)-Picrotoxinin", ChemRxiv (doi.org/10.26434/chemrxiv.9275318.v1), (Aug. 7, 2019), 7 pgs.

"International Application Serial No. PCT US2020 070376, International Search Report dated Apr. 26, 2021", 3 pages.

"International Application Serial No. PCT US2020 070376, Written Opinion dated Apr. 26, 2021", 5 pages.

Crossley, Steven W. M, "Synthesis of (−)-Picrotoxinin by Late-Stage Strong Bond Activation", Journal of the American Chemical Society vol. 142, No. 26, (Jun. 23, 2020), pp. 11376-11381.

* cited by examiner

*Primary Examiner* — Amanda L. Aguirre

(74) *Attorney, Agent, or Firm* — Schwegman Lundberg & Woessner, P.A.

(57) ABSTRACT

The present disclosure relates to concise processes for making (−)-picrotoxinin (1, PXN) and 5-methyl-picrotoxinin (20, 5MePXN), and to 5MePXN, its pharmaceutical compositions, and its method of use for inhibiting $GABA_A$ receptor.

7 Claims, 1 Drawing Sheet

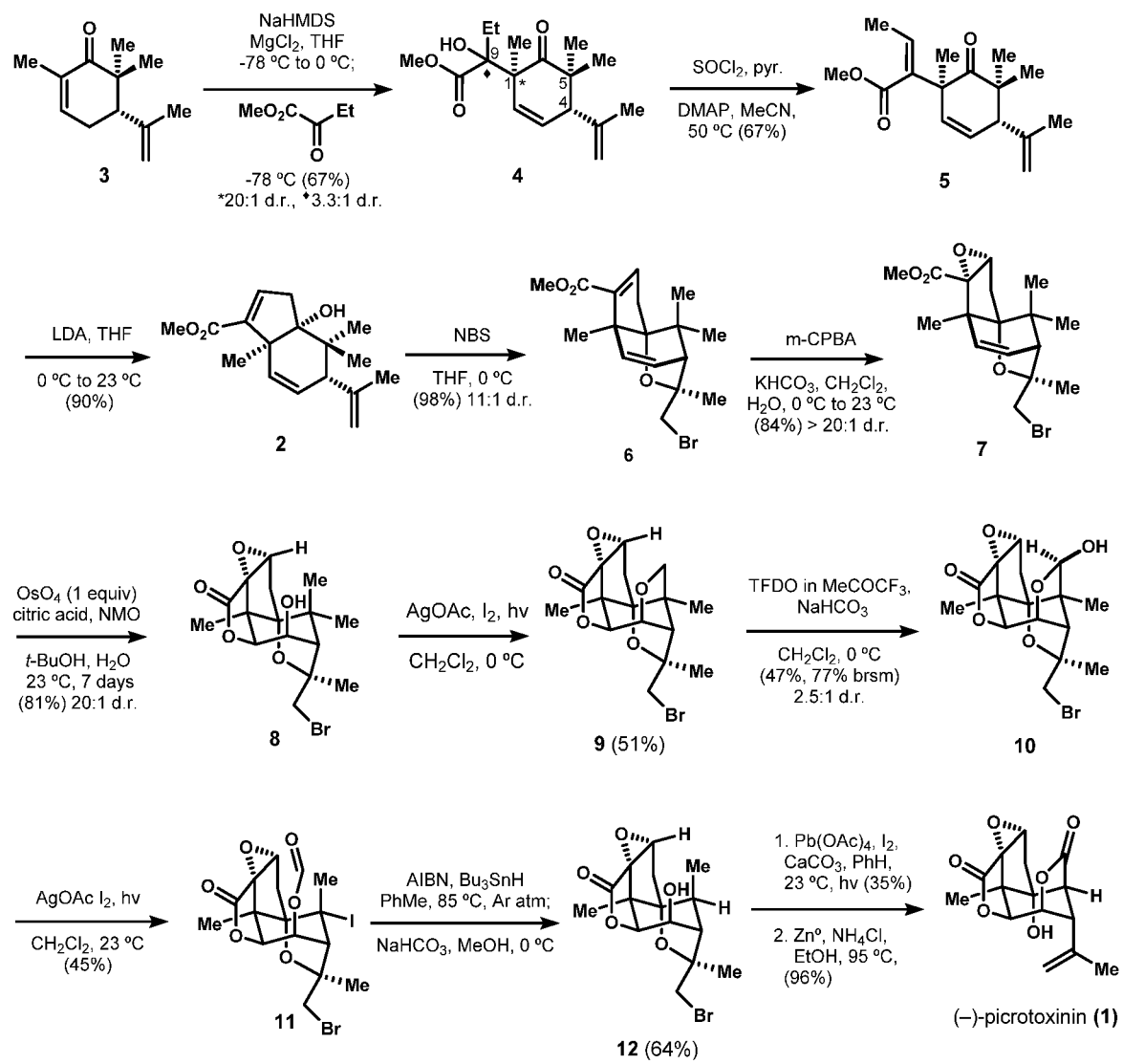

SHORT SYNTHESES OF (−)-PICROTOXININ AND RELATED COMPOUNDS

STATEMENT OF GOVERNMENT SUPPORT

This invention was made with government support under grant No. R35 GM122606 awarded by the National Institutes of Health. The U.S. government has certain rights in the invention.

BACKGROUND

Picrotoxinin (1, PXN) is the flagship member of the picrotoxane family of natural products and continues to attract considerable attention from the synthesis community[1-8] due to its stereochemically-dense poly oxygenated structure and its use as a tool compound in neuroscience.[9-11] Picrotoxin (PTX), which consists of an equimolar mixture of PXN and its less-active C12 hydrate, picrotin (PTN), can exhibit useful therapeutic properties: chronic dosing of Down's syndrome model mice (Ts65Dn) normalizes memory performance by reducing overactivity of GA-BAergic neurons.[12] However, the therapeutic window of PTX is narrow: lethal convulsion through hyperexcitatory $GABA_A$ receptor antagonism occurs at low dose ($LD_{50}$=2 mg/kg, rat, I.P.).[13] In contrast, $GABA_AR$ antagonists like bilobalide[14] can share the therapeutic properties, target, and binding site of PXN and yet avoid acute toxicity.[15] Further, 'neurotrophic' sesquiterpenes jiadifenolide[16] and O-debenzyltashironin[17] share the hyperexcitatory effects of convulsant $GABA_AR$ antagonists anisatin[17] and PXN, yet jiadifenolide displays no convulsive signature in mice.[15,18] A short synthetic route might allow interro-gation of analogs of PXN that similarly reduce its toxicity yet still antagonize GABAA receptors.[19]

The seminal work of Corey,[1,2] Yamada,[3] Yoshikoshi,[4] and Trost[5-7] illustrated the difficulty of the contiguous stereotetrad of 1. Intermolecular formation of this stereo-dense motif is challenged by the cis-fused orientation of the C7, C9, and C15 carbons, which arises biosynthetically by an anti-Markovnikov cationic cyclization of a cadinyl cation and oxidative cleavage.[20-21] Corey[1] and Yamada[3] employed intramolecular cyclization/C—C oxidative cleavage steps to overcome this problem, while Trost[5-7] leveraged torsional strain with a small nucleophile to set the C7/C15 stereodiad and a classic palladium-catalyzed cycloisomerization to make the C7/C9 junction. Yet all syntheses concede some C—C disconnections within and about the [4.3.0]-bicyclononane, rather than directly accessing the core by disconnections solely between the [4.3.0] ring junctions.

SUMMARY

The present disclosure addresses these needs and others by providing, in one embodiment, a process for making the compound (−)-picrotoxinin (1):

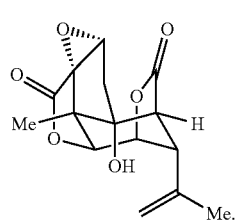

(1)

The process comprises the steps of:

(a1) subjecting compound (8) to etherification:

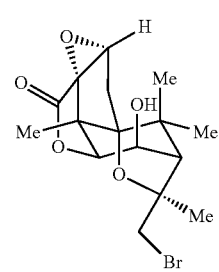

(8)

whereby compound (9) is formed:

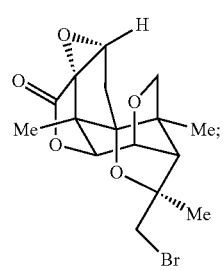

(9)

(a2) oxidizing compound (9) whereby compound (10) is formed:

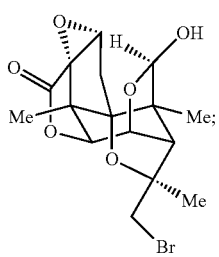

(10)

(a3) subjecting compound (10) to fragmentation whereby compound (11) is formed:

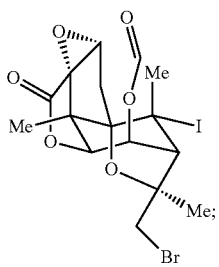

(11)

(a4) subjecting compound (11) to de-iodination and de-formylation whereby compound (12) is formed:

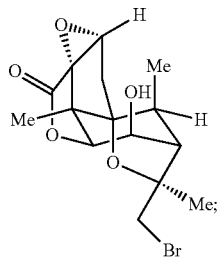
(12)

and (a5) subjecting compound (12) to sequential lactonization and reductive de-bromination whereby (−)-picrotoxinin (1) is formed.

The present disclosure provides in another embodiment a process for making the compound 5-methylpicrotoxinin (5MePXN) (20):

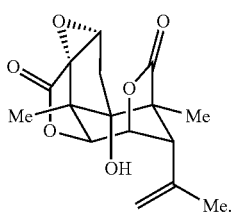
(20)

The process comprises the steps of:

(b1) subjecting compound (8) to oxidation:

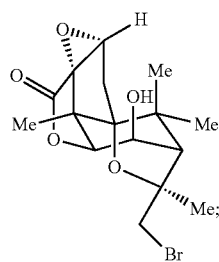
(8)

whereby compound (18) is formed:

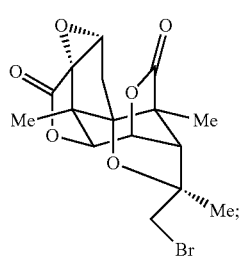
(18)

and (b2) subjecting compound (18) to reductive de-bromination whereby compound (20) is formed.

The present disclosure provides in an embodiment the compound 5MePXN (20):

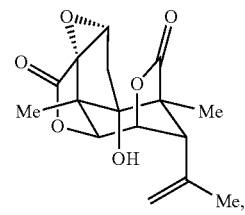
(20)

or a pharmaceutically acceptable salt thereof.

In another embodiment, the present disclosure provides a method for antagonizing $GABA_A$ receptor. The method comprises contacting the receptor with an effective amount of the compound (20) or a pharmaceutically acceptable salt thereof as described herein.

BRIEF DESCRIPTION OF THE DRAWINGS

FIG. 1: Synthetic scheme for making (−)-picrotoxinin (20).

DETAILED DESCRIPTION

The present disclosure provides a concise synthesis of (−)-picrotoxinin (1) via incorporation of a symmetrizing gem-dimethyl moiety that allows efficient annulation to form the [4.3.0]-bicyclononane core. One advantage of the synthetic methodology disclosed herein resides in the key stereotetrad being accessed in only 4 to 5 steps from (R)-carvone; hence, this advantage correlates to an overall short synthesis. For instance, the facile and stereoselective annulation to form compound (2) benefits from symmetrizing dimethylation, allowing stereochemical relay from the C4 β-isopropene of car one and obviating the need for stereocontrol at C5 (FIG. 1). Further, high oxidation states in the starting materials were encoded by unsaturation and leveraged to access compound (1) in the shortest sequence to date. The present disclosure provides the first synthetic route, to the inventors' knowledge, of an oxidative C—C demethylation sequence applied in total synthesis.

The present disclosure addresses these needs and others by providing, in one embodiment, a process for making the compound (−)-picrotoxinin (1):

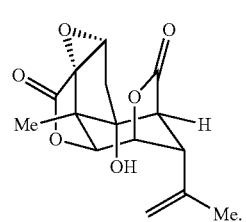
(1)

The process comprises the steps of
(a1) subjecting compound (8) to etherification:

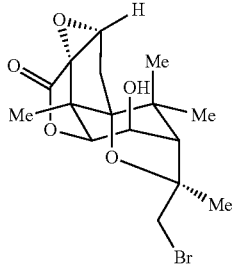
(8)

whereby compound (9) is formed:

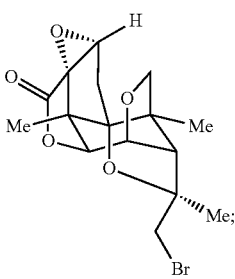
(9)

(a2) oxidizing compound (9) whereby compound (10) is formed:

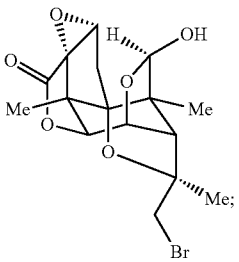
(10)

(a3) subjecting compound (10) to fragmentation whereby compound (11) is formed:

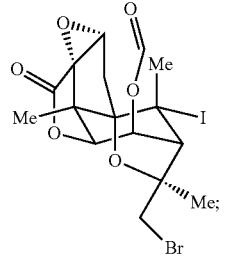
(11)

(a4) subjecting compound (11) to de-iodination and de-formylation whereby compound (12) is formed:

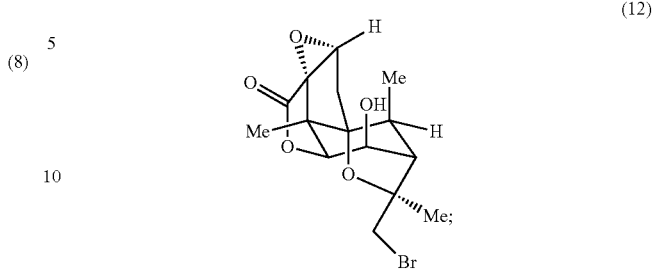
(12)

and
(a5) subjecting compound (12) to sequential lactonization and reductive de-bromination whereby (−)-picrotoxinin (1) is formed.

In an embodiment optionally in combination with any other embodiment herein described, the process further comprises the step of (a6) subjecting compound (1) to hydration whereby (−)-picrotin (19) is formed:

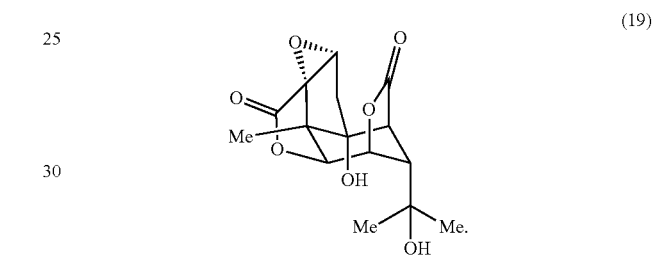
(19)

In another embodiment optionally in combination with any other embodiment herein described, the process further comprises steps (1) to (7) for making compound (8). Thus, in step (1), (R)-carvone (SI-1):

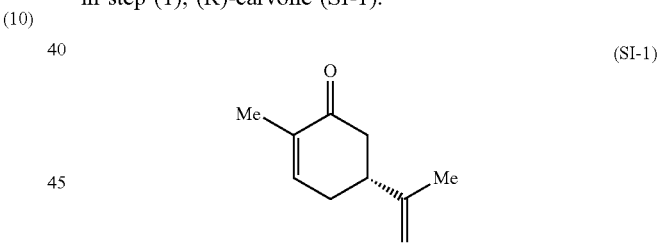
(SI-1)

is contacted with a methylating reagent whereby compound (3) is formed:

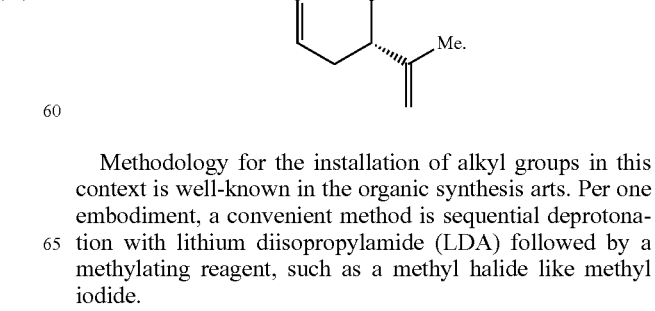
(3)

Methodology for the installation of alkyl groups in this context is well-known in the organic synthesis arts. Per one embodiment, a convenient method is sequential deprotonation with lithium diisopropylamide (LDA) followed by a methylating reagent, such as a methyl halide like methyl iodide.

In step (2), compound (3) is subjected to aldol addition with methyl-2-oxobutanoate whereby compound (4) is formed:

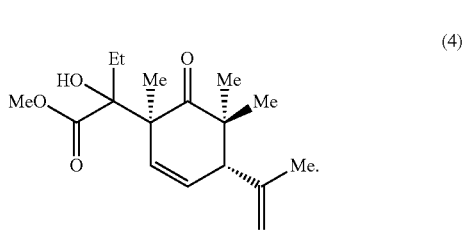

(4)

In step (3), compound (4) is subjected to dehydration whereby compound (5) is formed:

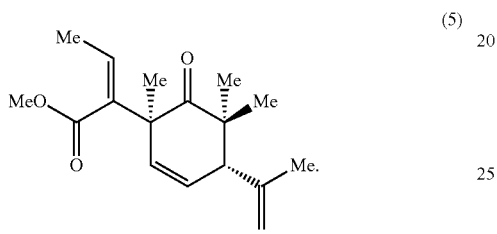

(5)

In some embodiments, the dehydration is achieved by contacting compound (4) with thionyl chloride ($SOCl_2$).

In step (4), compound (5) is subjected to intramolecular aldol addition whereby compound (2) is formed:

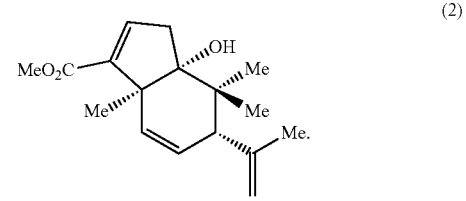

(2)

In an embodiment, the intramolecular aldol addition comprises contacting compound (2) with a non-nucleophilic base. For example, the non-nucleophilic base is a sterically bulky non-nucleophilic base, such as LDA.

In step (5), according to an embodiment, compound (2) is subjected to bromination and etherification whereby compound (6) is formed:

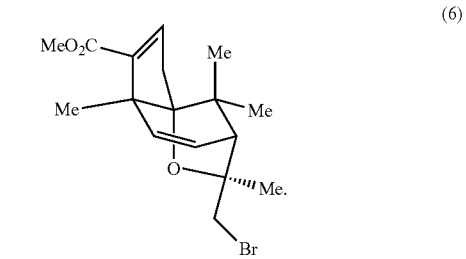 [SMILES: COC(=O)C1=CCC23O[C@](C)(CBr)C(C=CC12C)C3(C)C]

(6)

In one embodiment, the bromination and etherification comprise contacting compound (2) with $Br_2$. For example, a useful source of formal $Br_2$ is N-bromosuccinimide (NBS).

In step (6), per an additional embodiment, compound (6) is subjected to epoxidation conditions whereby compound (7) is formed:

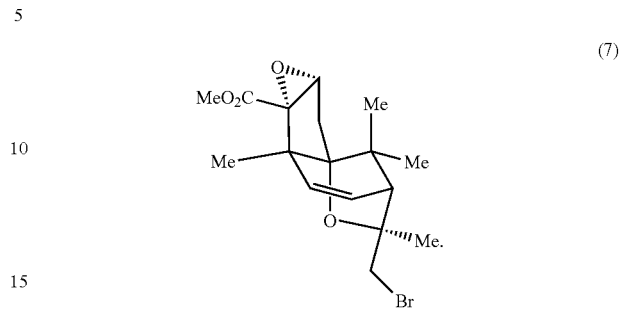

(7)

In step (7), compound (7) is subjected to hydroxylation conditions whereby compound (8) is formed by dihydroxylation.

In various embodiments, optionally in combination with any other embodiment herein described, the etherification in step (a1) comprises contacting compound (8) with iodine monoacetate. Iodine monoacetate (MAO is provided by various reagents known in the art.[33] Thus, for example, iodine ($I_2$) is combined with silver acetate (AgOAc) or lead (IV) acetate ($Pb(OAc)_4$) in a solvent at temperatures ranging from about 0° C. to about 25° C. Illustrative solvents include hydrocarbons such as benzene and cyclohexane, and chlorinated solvents such as methylene chloride ($CH_2Cl_2$) and $CCl_4$. Useful sources of IOAc for this step and others described herein, per some embodiments, and illustrated in the examples below, reside in a combination of AgOAc/$I_2$ in $CH_2Cl_2$ or $Pb(OAc)_4$ in benzene under ambient light.

In step (a2), in accordance with an embodiment optionally combined with any other embodiment here described, the oxidizing comprises contacting compound (9) with methyl (trifluoromethyl)dioxirane.

In step (a3), in accordance with an embodiment optionally combined with any other embodiment here described, the fragmentation comprises contacting compound (10) with iodine monoacetate. Exemplary sources of iodine monoacetate are described herein.

In step (a4), in accordance with an embodiment optionally combined with any other embodiment here described, the de-iodination and de-formylation comprise contacting compound (11) with tributyltin hydride followed by basic workup. De-iodination can be achieved, in various embodiments, by use of a radical initiator and hydrogen-atom donor. A convenient radical initiator is exemplified by azobisisobutyronitrile (AIBN). Various stannanes known in the art can be used to achieve chemoselective replacement of iodine with hydrogen, such as triphenyltin hydride and tributyltin hydride.

In step (a5), in accordance with an embodiment optionally combined with any other embodiment here described, the lactonization comprises contacting compound (12) with iodine monoacetate, such as obtained by the reagents and conditions described herein. Methodology for subsequent reductive de-bromination is well-known in the art. An illustrative route is achieved by use of zinc(0) and $NH_4Cl$.

The present disclosure provides in another embodiment a process for making the compound 5MePXN (20), a formal (−)-picrotoxinin analog that bears a methyl group at the 5-position:

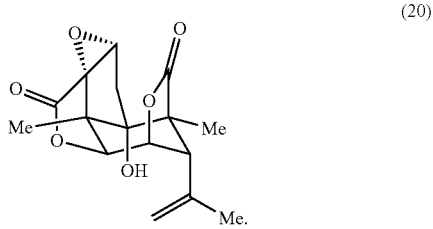
(20)

The process comprises the steps of
(b1) subjecting compound (8) to oxidation:

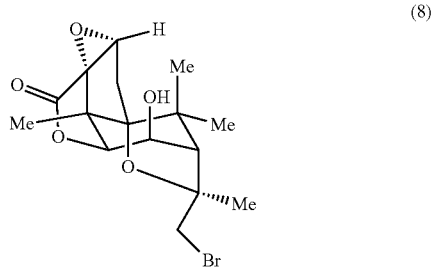
(8)

whereby compound (18) is formed:

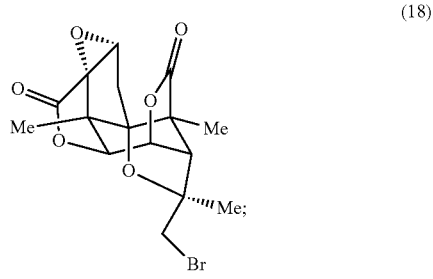
(18)

and
(b2) subjecting compound (18) to reductive de-bromination whereby compound (20) is formed.

In various embodiments, optionally in combination with any other embodiment, in step (b1), the oxidation comprises contacting compound (8) with iodine monoacetate. Reagents and conditions for generating iodine monoacetate are described herein.

In various embodiments, optionally in combination with any other embodiment, in step (b2), the reductive de-bromination comprises contacting compound (18) with zinc (0)/$NH_4Cl$).

Illustrative and non-limiting embodiments of the present disclosure reside in the following additional description of the processes disclosed herein. The inventors encoded the oxidations of compound (1) with alkenes to arrive at carbocycle (2), which might derive from (R)-carvone[1,3,5,22] via annulation of methyl-2-oxo-butanoate. Most oxidation patterns were embedded into starting materials,[23] with the exception of the C15 carboxylate. The decision to decrease C15 to the methyl oxidation state was informed by problems encountered in the literature[47,9·11] with C10/C15 translactonization and intramolecular epoxide opening at higher oxidation states of C15. However, it was surprisingly discovered that a single methyl group on carvone led to the incorrect stereoisomer. Instead, it was discovered that geminal dimethylation enabled efficient synthesis of compound (2) in only four steps. The challenge then became discovery of a late-stage, stereoselective, cleavage of a strong C—C bond—a counterintuitive[24] but, in this case, enabling tactic for a concise synthesis of compound (1) (FIG. 1).

Dimethylation of (R)-carvone was achieved in one[25] or two[26] steps, although the latter procedure was employed on 30 g (200 mmol) scale. The magnesium enolate of compound (3) was formed by deprotonation with NaHMDS in the presence of anhydrous $MgCl_2$; subsequent addition of methyl-2-oxobutanoate at −78° C. gave the aldol addition product compound (4) in 67% yield with excellent diastereoselectivity (>20:1) at C1 and inconsequential 3.3:1 diastereoselectivity at C9. Use of lithium, sodium, potassium, or zinc enolates gave diminished to no yield of compound (4). The reaction was quenched at −78° C. to avoid retro-aldol decomposition that occurs above −20° C. This unusual aldol reaction occurs with high regio- and diastereoselectivity to form a quaternary carbon (C1) and a neopentyl alcohol (C9).

Replacing one of the Me groups with Br, Cl, or CN groups yielded poor stereo-control in formation of the C5 stereocenter and subsequent failure of the aldol addition through proton-transfer, elimination and aromatization pathways. Surprisingly, it was not possible to achieve symmetrical substitution at C5 with silylhydroxymethylene ($R_3SiOCH_2$—),[6] methyl ester, or nitrite groups in the aldol addition. Because the inclusion of an extra C5 methyl group enabled installation of all 15 carbon atoms of the picrotoxinin skeleton with the correct regio- and stereochemistry in just two steps and without need for C5 stereo-control, the processes disclosed herein relied upon a risky but successful excision of the extra C5 methyl group at a late stage.

Neopentyl alcohol (4) was converted to compound (5) by a $SOCl_2$-induced elimination.[27] These conditions surprisingly eliminated both diastereomers of the sterically congested C9 alcohol 4. A vinylogous intramolecular 5-exo-trig aldol addition reaction yielded compound (2) in 90% yield upon treatment of compound (5) with LDA at 0° C. and warming to 23° C.

Facile and scalable access to compound (2) allowed extensive interrogation of the remaining alkene oxidations. First, bromoetherification[1,5,9] with NBS proved entirely selective for the isopropene group and delivered an 11:1 diastereomeric mixture of compound (6). This dual-purpose bromoetherification served to protect the $\Delta^{12,13}$ isopropenyl alkene and lock the conformation of compound (2) to promote lactonization at C10 and directed oxidation of the C5 methyl groups. Epoxidation of compound (6) initially suffered poor diastereocontrol under nucleophilic epoxidation conditions e.g. alkali metalperoxides) and low conversion with electrophilic epoxidation reagents (e.g. DMDO, trifluoroperacetic acid). Although mCPBA alone was insufficient to react with compound (6), it was found that use of $KHCO_3$ with mCPBA in a biphasic mixture of $CH_2Cl_2$ and $H_2O$ at 23° C. afforded compound (7) with high diastereoselectivity in 84% yield. It was surmised that dihydroxylation of compound (7) might be facile by analogy with Yoshikoshi's $OsO_4$/pyridine oxidation of a similar substrate,[4] but no more than 30% conversion could be obtained under these conditions (stoichiometric $OsO_4$, pyridine).

Thus, it was discovered that addition of citric acid to prevent off-pathway osmium sequestration[28] enabled full conversion of compound (7) to compound (8). Steric congestion about the $\Delta^{2,3}$ alkene of compound (7), however, slowed conversion such that one equivalent of $OsO_4$ still required 7 days to elicit an 81% yield.[29] This drawback was mitigated by excellent diastereoselectivity (>20:1) at C2 and C3 and spontaneous lactonization at C10. For comparison, the strong oxidant dimethyldioxirane reacted exclusively with the electron-deficient $\Delta^{8,9}$ alkene in compound (6) to provide compound (7), which did not react further.

Compound (8) provides the opportunity for gem-dimethyl modification, including C—C bond cleavage. Geminal dimethyl groups predominate in terpenoids as a result of their biosynthesis from polyprenyl-(dimethylallyl) pyrophosphates.[30] Modification of gem-dimethyls, including their excision, can be effected with iron-oxo enzymes to produce biologically active scaffolds.[31] Similar demethylations have not been employed in chemical synthesis because abiotic routes are not often constrained by biosynthetic building blocks, and because retrosynthetic addition of an extra carbon-bound methyl group is seldom simplifying.[32] The presently described process, however, is an exception to the rule.

It was possible to directly access the primary (e.g., ether 9), secondary (acetal), or tertiary (lactone) oxidation states of the axial methyl group in compound (8) by generating IOAc[33] with different reagents and temperatures. Thus, use of $AgOAc/I_2$ in methylene chloride at 23° C. under ambient light provided compound (9) in 51% yield (FIG. 1), whereas the primary iodide was instead obtained at 0° C. in cyclohexane as the major product. Treatment of compound (9) with methyl(trifluoromethyl)dioxirane (TFDO) at 0° C. generated hemiacetal 9 as a 2.5:1 diastereomeric mixture, a distribution which may be attributed to the outward-facing C—H bond being both less sterically hindered and experiencing better hyperconjugative donation from the C3 ether oxygen than its inward-facing counterpart. Conditions applied here (AgOAc, $I_2$, $CH_2Cl_2$, 23° C.) led to Suarez fragmentation[34] in compound (10) of the adjacent strong C—C bond to form compound (11) as a single stereoisomer. The tertiary iodide of compound (11) was removed with $AIBN/Bu_3SnH$ to form a single isomer as compound 12 after cleavage of the formyl group in a basic work-up. Use of $Pb(OAc)_4/I_2$, in benzene with $CaCO_3$ at 23° C. under an aerobic atmosphere led directly to formation of the C15 lactone. Reduction with zinc cleaved the bromoether linkage of compound (12) to deliver (−)-picrotoxinin (1). Conversion to (−)-picrotin (19) occurred in one step and 84% yield by a Mukaiyama hydration,[35] which had not been reported previously.[2,4,6,7]

Geminal dimethylation of carvone at C5 expedited forward entry to the carbocyclic core of PXN. The complexity of compound (1) versus compound (20) was not diminished by methylation because information content was added and no stereocenter was removed ($C_m$=468 vs. 480 mcbits).[36] Symmetrization of C5 in intermediate targets like compound (8), however, greatly simplified entry into chemical space very close to compound (1). As further described in the appended examples, 5-methyl-picrotoxinin (20) retained modest antagonism of the $GABA_A$ receptor ($IC_{50}$=9 μM; vs. [$^3$H] TBOB @ at cerebral cortex) and slightly improved upon the aqueous stability of compound (1) at pH 8, more than halving the pseudo-first order rate constant.

The present disclosure also provides in an embodiment the compound 5MePXN (20):

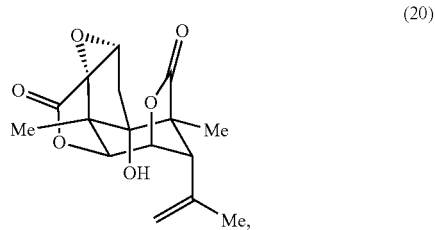

or a pharmaceutically acceptable salt thereof.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

Pharmaceutical Composition

The present disclosure provides in another embodiment a pharmaceutical composition comprising a compound or pharmaceutically acceptable salt thereof as described herein in combination with a pharmaceutically acceptable carrier or excipient.

Compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of the compound or a pharmaceutically acceptable salt thereof.

For tablet compositions, the compound or a pharmaceutically acceptable salt thereof in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, the compound or a pharmaceutically acceptable salt thereof is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compound or a pharmaceutically acceptable salt thereof in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the compound or a pharmaceutically acceptable salt thereof in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound the compound or a pharmaceutically acceptable salt thereof may also be administered in the form of suppositories for rectal administration. These compositions can be prepared by mixing the compound with a suitable non-irritating excipient which is solid at ordinary temperatures but liquid at the rectal temperature and will therefore melt in the rectum to release the compound. Exemplary excipients include cocoa butter and polyethylene glycols.

Compositions for parenteral administrations are administered in a sterile medium. Depending on the vehicle used and concentration the concentration of the compound or a pharmaceutically acceptable salt thereof in the formulation, the parenteral formulation can either be a suspension or a solution containing dissolved compound. Adjuvants such as local anesthetics, preservatives and buffering agents can also be added to parenteral compositions.

Method of Use

In additional embodiments, the present disclosure provides a method for antagonizing $GABA_A$ receptor. The method comprises contacting the receptor with an effective amount of the compound (20) or a pharmaceutically acceptable salt thereof, as described herein. In one embodiment, the contacting occurs in vitro, such as by contact of the compound to a neuron.

In another embodiment, the contacting occurs in vivo, such as achieved by administering the compound to a patient in need of $GABA_A$ antagonism. The administration can be achieved by any of the routes of administration described herein.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent. A therapeutically effective amount also is the minimum amount necessary to antagonize the $GABA_A$ receptor.

Generally, the initial therapeutically effective amount of a compound described herein or a pharmaceutically acceptable salt thereof that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of the compound or a pharmaceutically acceptable salt thereof in another embodiment, such dosage forms contain from about 50 mg to about 500 mg of the compound or a pharmaceutically acceptable salt thereof. In yet another embodiment, such dosage forms contain from about 25 mg to about 200 mg of the compound or a pharmaceutically acceptable salt thereof. In still another embodiment, such dosage forms contain from about 10 mg to about 100 mg of the compound or a pharmaceutically acceptable salt thereof in a further embodiment, such dosage forms contain from about 5 mg to about 50 mg of the compound or a pharmaceutically acceptable salt thereof. In any of the foregoing embodiments the dosage form can be administered once a day or twice per day.

The following non-limiting examples describe additional embodiments of the present disclosure.

EXAMPLES

Materials and Methods. Pentane, hexanes, dichloromethane (DCM), toluene, ethyl acetate (EtOAc), diethyl ether, benzene, dimethylsulfoxide (DMSO), methanol (MeOH), N-dimethylformamide (DMF), dichloroethane (DCE), α, α, α-trifluorotoluene and triethylamine were purchased from Sigma Aldrich, EMD Chemicals, Fisher Chemicals or Acros Organics and used without further purification. All anhydrous solvents were purchased from Fisher Chemicals, Sigma Aldrich or Acros Organics and used without further purification, unless otherwise stated. Reactions were monitored by thin layer chromatography (TLC) with precoated silica gel plates from EMD Chemicals (TLC Silica gel 60 F254, 250 μm thickness) using UV light as the visualizing agent and an acidic mixture of anisaldehyde, phosphomolybdic acid (PMA), chromic acid, iodine vapor, Seebach's stain, or basic aqueous potassium permanganate ($KMnO_4$), and heat as developing agents. Preparatory thin layer chromatography (PTLC) was performed using the aforementioned silica gel plates. Flash column chromatography was performed over silica gel 60 (particle size 0.035-0.07 mm) from Acros Organics.

NMR spectra were recorded on Bruker DRX-600 (equipped with a 5 mm DCH Cryoprobe), AV-600, DRX-500 or DPX-400 and calibrated using residual non-deuterated solvent as an internal reference ($CHCl_3$ @ 7.26 ppm $^1H$ NMR, 77.16 ppm $^{13}C$ NMR; $(CD_3)_2CO$ @ 2.05 ppm $^1H$ NMR, 206.26 ppm $^{13}C$ NMR). The following abbreviations (or combinations thereof) were used to explain the multiplicities: s=singlet, d=doublet, t=triplet, q=quartet, p=pentet, sex=sextet, sep=septet m=multiplet, br=broad. LC/MS analysis was performed on an Agilent 1200 series HPLC/MS equipped with an Agilent SB-C18 2.1 mm×50 mm column, with mass spectra recorded on a 6120 Quadrupole mass spectrometer (API-ES), using ACN and $H_2O$ as the mobile phase (0.1% formic acid). LC/MS runs used the following method unless otherwise specified: flow rate of 0.5 mL/min is used, initial equilibration of 5% $ACN/H_2O$ with a linear gradient to 95% $ACN/H_2O$ over 5 minutes, then a hold at 95% $ACN/H_2O$ for an additional 3 minutes. GC/MS analysis was performed on Agilent 7820A/5975 GC/MSD system with helium as a carrier gas. Unless otherwise specified, GC/MS runs were performed with the following method: GC/MSD; HP-5MS (30 m×0.25 mm. ID, part #19091S-433); 139 KPa; flow rate 2 mL/min; inlet temperature 250° C.; column temperature 50° C. for 0 min, then 20° C./min to 280° C., then held for 2 min. GC/FTD analysis was conducted on an Agilent 7820A GC/FID system with nitrogen as a carrier gas and with air and hydrogen as combustion gasses. Unless otherwise specified, GC/FID runs were prepared with the following method: GC/FID; HP-5MS UI (20 m×0.180 mm ID, part 190915-577UI); inlet temperature 250° C.; column temperature 50° C. for 0 min, then 20° C./min to 280° C., then held for 2 min. Chiral HPLC analysis was performed on Agilent 1100 series equipped with a DAL) detector. Chiralcel OZ-3, 3 μm particle size, 250 mm×6 mm column; flow rate 1 mL/min with solvent mixture of 98% hexanes and 2% isopropanol; detection wavelength 210 nm. Optical rotations of arylated menthol derivatives were measured digitally on an Autopol III polarimeter from Rudolph Research Analytic, using a flow cell with a 0.5 decimeter pathlength and the sodium lamp D-line wavelength (λ=589.3 nm). High resolution mass spectrometric data were obtained on a Waters Xevo G2-XS TOF instrument (http://www.waters.com/webassets/cms/library/docs/720005089en.pdf). Calculated HRMS data were obtained by input of the (M+H) chemical formulae into the Exact Mass Calculator, Single Isotope Version at (https://www.sisweb.com/referenc/tools/exactmass.htm?formula).

Unless otherwise noted, all experiments were run in flame-dried glassware under an atmosphere of argon gas.

Example 1: Dimethyl-Carvone (3) Formation

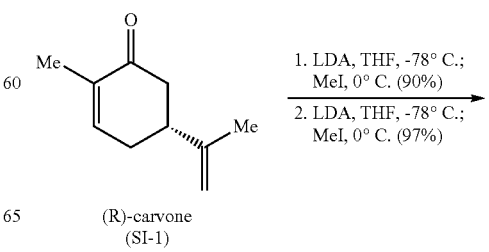

(R)-carvone
(SI-1)

1. LDA, THF, -78° C.;
   MeI, 0° C. (90%)
2. LDA, THF, -78° C.;
   MeI, 0° C. (97%)

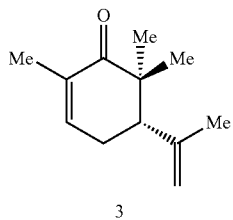

3

A [0.33 M] solution of LDA in THF was formed by addition of nBuLi in hexanes [2.67 M] (1.2 equiv, 240.0 mmol, 90 mL) to a solution of diisopropylamine (distilled off CaH$_2$) (1.5 equiv, 300.0 mmol, 42.0 ml) in THF (600 mL, [0.5 M] wrt HN$^i$Pr$_2$) at −78° C. After addition, the solution was stirred at 0° C. for 30 minutes before cooling back to −78° C.

To a flame-dried 500 mL round bottom flask containing a [0.33 M] solution of LDA in THF (1.2 equiv, 240.0 mmol, see above for preparation details) cooled to −78° C. in a dry ice/acetone bath under an argon atmosphere was added via cannula a [1M (ignoring carvone volume)] solution of (R)-carvone (SI-1) (1 equiv, 200.0 mmol, 30 g, 31.3 mL) in THF (200 mL). The addition took 10 minutes and the solution turned from clear and pale yellow to yellow over the course of the addition. The reaction was allowed to stir for 105 minutes, at which point methyl iodide (2.0 equiv, 200.0 mmol, 12.4 mL) was added neat in a slow but steady stream to the carvone enolate solution. The reaction was then stirred at 0° C. in an ice water bath and monitored by TLC (5% EtOAc/hex). Full consumption of can/one was observed after 60 minutes.

After completion, the reaction was quenched by pouring the reaction onto a 1:1 mixture of saturated NH$_4$Cl (aq.):H$_2$O (500 mL). The aqueous layer was extracted with EtOAc (3× ~250 mL). The organic layer was washed 1× each with Na$_2$S$_2$O$_3$ (saturated, aq.~250 mL) and brine (saturated, aq.~250 mL), and then dried over MgSO$_4$, filtered, and concentrated. A white precipitate crashed out of the solution during concentration on the rotovap (presumably a diisopropylamine HI salt). The solid was filtered off over a plug of celite, rinsing with hexanes. The yellow solution became increasingly yellow/orange upon concentration. Therefore, the solution was diluted in 500 mL of hexanes, washed 1× with Na$_2$S$_2$O$_3$ (saturated, aq., 100 mL) which removed most of the yellow color, dried over MgSO$_4$, filtered and concentrated. The crude residue was purified by fractional distillation on high vacuum. The desired mixture of α-methyl-carvone isomers was distilled over as a colorless to slightly pale-yellow oil at ~125-130° C. (external temperature), ~90-91° C. (internal temperature at distillation head) at a pressure of <5 torr. α-methyl-carvone (1:1 cis:trans) was obtained 90% yield (29.4 g, 180.0 mmol).

A second [0.34 M] solution of LDA in THF was formed by addition of nBuLi in hexanes (1.25 equiv, 225.0 mmol, 84 mL of [2.67 M]) to a solution of diisopropylamine (distilled off CaH$_2$) (1.5 equiv, 270.0 mmol, 37.7 ml) in THF (540 mL, [0.5 M] with respect to HN$^i$Pr$_2$) at −78° C. After addition, the solution was stirred at 0° C. for 30 minutes before cooling back to −78° C.

To a flame-dried 500 mL round bottom flask containing the [0.34 M] solution of LDA in THF (1.2 equiv, 108.0 mmol, see above for preparation details) cooled to −78° C. in a dry ice/acetone bath under an argon atmosphere was added via cannula a [1M (ignoring α-methyl-carvone volume)] solution of α-methyl-carvone (1 equiv, 180.0 mmol, 29.4 g) in THF (180 mL). The substrate solution was rinsed with a few mL of anhydrous THF after transfer. The solution was allowed to stir for 90 minutes, at which point methyl iodide (2.0 equiv, 180.0 mmol, 11.2 mL) was added neat in slow but steady stream to the α-methyl-carvone enolate solution. The reaction was then stirred at 0° C. in an ice water bath and monitored by TLC (10% EtOAc/hex). After 1 hour, some starting material still remained by TLC (10% EtOAc/hex). After two hours, there appeared to be no further conversion, so the solution was quenched.

The reaction was poured onto a 1:1 mixture of saturated NH$_4$Cl (aq.):H$_2$O (500 mL). The aqueous layer was extracted with EtOAc (1× ~250 mL) and hexanes (2× ~250 mL). The organic layer was washed 1× each with Na$_2$S$_2$O$_3$ (saturated, aq., ~250 mL) and brine (saturated, aq., ~250 mL) and then dried over MgSO$_4$, filtered, and concentrated. The residue turned increasingly yellow (NOTE 1) and cloudy during concentration, so the residue was dissolved in ~150 mL of hexanes and washed a second times with Na$_2$S$_2$O$_3$ (saturated, aq., ~100 mL). After separation, the organic layer was dried over MgSO$_4$, filtered, and concentrated in vacuo. The reaction was purified by a fractional distillation on high vacuum. Dimethyl-carvone was distilled over as a colorless to slightly pale-yellow oil at 120-130° C. (external temperature), ~80° C. (internal temperature at distillation head) at a pressure of <5 torr. α-methyl-carvone was obtained in 97% yield (31.1 g, 174.0 mmol). NMR analysis indicated a 1.00:0.03:0.03 mixture of dimethyl-carvone to α-methyl-carvone isomers. This compound was used without further purification in the subsequent step and stored over solid copper in a tinted glass bottle (old CDCl$_3$ bottle) away from light at −20° C.

Characterization of dimethyl-carvone (3): R$_f$ 0.44 in 5% EtOAc/hex, 0.56 in 10% EtOAc/hex. Stains purple in anisaldehyde. Opt. Rot. α$_{obs}$=−10.7°, c=1.00 in CH$_2$Cl$_2$, T=22.9° C. $^1$H NMR (600 MHz, Chloroform-d) δ 6.61 (ddt, J=6.2, 2.8, 1.4 Hz, 1H), 4.86 (p, J=1.6 Hz, 1H), 4.77-4.65 (m, 1H), 2.53 (dd, J=7.7, 5.4 Hz, 1H), 2.49-2.42 (m, 1H), 2.44-2.35 (m, 1H), 1.77 (q, J=1.8 Hz, 3H), 1.72-1.66 (m, 3H), 1.14 (s, 3H), 1.03 (s, 3H). $^{13}$C NMR (151 MHz, Chloroform-d) δ 204.7, 146.1, 142.4, 133.7, 113.9, 52.2, 44.8, 29.2, 24.6, 23.5, 20.5, 16.6. HRMS Calculated C$_{12}$H$_{19}$O [M+H]: 179.1436. Found: 179.1432.

Example 2: Aldol Addition of Methyl-2-Oxobutanoate to 3 to Form 4

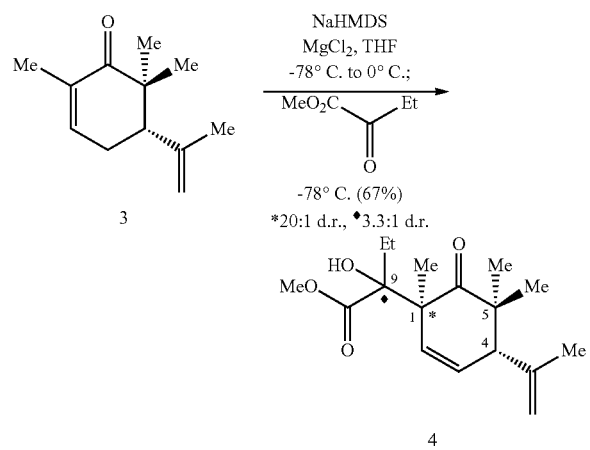

To a flame-dried round bottom flask charged with anhydrous MgCl$_2$ (1.9 g, 20.0 mmol, 2 equiv, NOTE 1) was added a solution of freshly distilled dimethyl-carvone 3 (1.78 g, 10.0 mmol, 1 equiv) in anhydrous THF (100 mL) at 23° C. for 20 minutes. NaHMDS (1 M in THF, 15 mL, 15.0 mmol, 1.5 equiv) was added to the above mixture at −78° C. The reaction was vigorously stirred for an additional 30 minutes at −78° C. The solution was placed in a 0° C. ice/water bath and stirred for 60 minutes at 0° C. Once the enolate was fully formed (NOTE 2), the solution was cooled back to −78° C. and methyl-2-oxobutanoate (3.35 mL, 30.0 mmol, 3.0 equiv) was added neat to the enolate solution in a steady stream within a period of 5 minutes. After 75 minutes, the mixture was quenched by addition of saturated NH$_4$Cl/H$_2$O (1:1, v:v, 20 mL) at −78° C. (NOTE 3). The reaction was then warmed to room temperature and extracted with EtOAc (3×150 mL). The organic layer was washed with brine, dried over Na$_2$SO$_4$, filtered, and concentrated in vacuo. The crude residue was purified by flash column chromatography over silica gel (5% EtOAc/hex to 10% EtOAc/hex). The desired aldol addition products 4 were collected together (1.91 g, 6.7 mmol, 67%, dr~3.3:1 at C-9, NOTE 4) as a pale-yellow oil.

NOTE 1: MgCl$_2$ powder (weighed out assuming it is anhydrous) further dried by heating with a heat gun wider high vacuum until no more 'bubbling' of the powder occurs. The vessel is then placed under an argon atmosphere and other reagents are added to this reaction vessel.

NOTE 2: After 60 minutes, it is useful to TLC the enolate solution to confirm that the enolate has fully formed. Protonation at C-1 occurs upon TLC analysis to give the deconjugated isomer of dimethyl-carvone, which is less polar than dimethyl-carvone and not UV-active. Disappearance of the dimethyl-carvone spot is observed when the enolate has fully formed.

NOTE 3: The reaction must be quenched at −78° C. because the retro-aldol reaction of the product occurs at warmer temperatures (ca>~−20° C.).

NOTE 4: The yield of this reaction between different runs ranged from 60-70% and the diastereoselectivity between 2-3.3:1 at the C-9 alcohol. The opposite diastereomer at C-1 was never observed. The C-9 diastereomers can be collected separately after chromatographic separation. A 2.2:1 diastereomeric mixture at C-9 were separated and used for characterization of the two C-9 diastereomers.

Characterization data of aldol addition adduct (4, major diastereomer): R$_f$ 0.23 in 15% EtOAc/hex. Weakly UV active. Stain purple in anisaldehyde. Opt. Rot. α$_{obs}$=+58.9°, c=1.00 in CH$_2$Cl$_2$, T=25.6° C. $^1$H NMR (600 MHz, Chloroform-d) δ 5.91 (dd, J=10.3, 2.4 Hz, 1H), 5.80 (dd, J=10.3, 3.1 Hz, 1H), 5.05 (dq, J=2.0, 1.3 Hz, 1H), 4.77 (dt, J=1.7, 0.8 Hz, 1H), 3.87 (s, 3H), 3.76 (s, 1H), 3.15 (t, J=2.8 Hz, 1H), 1.98 (dq, J=13.7, 7.3 Hz, 1H), 1.81 (dd, J=1.5, 0.8 Hz, 3H), 1.67 (dq, J=13.6, 7.4 Hz, 1H), 1.34 (s, 3H), 1.11 (s, 3H), 1.02 (s, 3H), 0.76 (t, J=7.3 Hz, 3H). $^{13}$C NMR (151 MHz, Chloroform-d) (δ 218.4, 176.1, 144.7, 132.9, 130.6, 115.9, 83.3, 55.0, 53.0, 50.2, 48.4, 26.6, 24.7, 23.1, 23.0, 22.0, 7.6. HRMS Calculated C$_{17}$H$_{27}$O$_4$ [M+H]: 295.1909|Found: 295.1906.

Characterization data of aldol addition adduct (4, minor diastereomer): R$_f$0.3 in 15% EtOAc/hex. Weakly UV active. Stain purple in anisaldehyde. Opt. Rot. α$_{obs}$=−45.9°, c=1.00 in CH$_2$Cl$_2$, T=24.2° C., $^1$H NMR (600 MHz, Chloroform-d) δ 5.86 (dd, J=10.3, 2.3 Hz, 1H), 5.52 (dd, J=10.4, 3.2 Hz, 1H), 5.11-4.98 (m, 1H), 4.75 (dq, J=1.7, 0.8 Hz, 1H), 4.09 (d, J=1.6 Hz, 1H), 3.76 (s, 3H), 3.18 (t, J=2.8 Hz, 1H), 2.11 (dq, J=14.6, 7.3 Hz, 1H), 1.90 (dq, J=14.7, 7.4 Hz, 1H), 1.84-1.78 (m, 3H), 1.32 (s, 3H), 1.13 (s, 3H), 0.99 (s, 3H), 0.79 (t, J=7.3 Hz, 3H). $^{13}$C NMR (151 MHz, Chloroform-d) δ 218.5, 175.2, 144.7, 133.1, 130.4, 116.0, 84.3, 52.7, 52.4, 50.2, 48.5, 26.0, 24.5, 23.2, 22.6, 22.4, 8.1. HRMS (M+H) Calculated C$_{17}$H$_{27}$O$_4$ [M+H]: 295.1909|Found: 295.1905.

Example 3: Dehydration of 4 to Form 5

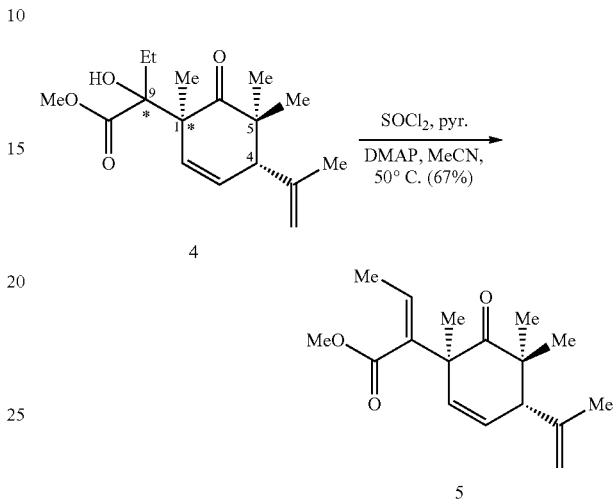

Two separate solutions were made: First, a solution of diastereomeric (3.3:1 d.r) substrate 4 (1.47 g, 5.0 mmol, 1.0 equiv), DMAP (3.05 g, 25.0 mmol, 5.0 equiv), and non-anhydrous MeCN (50 mL, [0.1 M] with respect to substrate) was made in a 250 mL round bottom flask. Second, a solution of SOCl$_2$ (725 μL, 10.0 mmol, 2 equiv) in anhydrous pyridine (10 mL, [1 M] with respect to SOCl$_2$) under an argon atmosphere was made. The substrate/DMAP/MeCN solution was slowly added SOCl$_2$/pyr solution with vigorous stirring at 50° C. (oil bath). The reaction was monitored by TLC. After 45 minutes, the resulting orange solution was cooled to room temperature, then poured onto a 1:1 mixture of H$_2$O:EtOAc (50 mL each). The aqueous layer was extracted with EtOAc (3×50 mL). The combined organic layer was washed with 1 M HCl (20 mL), saturated NaHCO$_3$ (20 mL), and brine. The combined organic layer was dried over Na$_2$SO$_4$, filtered and concentrated in vacuo. The crude residue was purified by flash column chromatography over silica gel (5% EtOAc/hex to 10% EtOAc/hex) to obtain elimination product 5 (926 mg, 3.35 mmol, 67%) as a clear yellow oil.

NOTE: Toluene may be substituted for MeCN, but the reaction takes~12 hours for a similar result.

Characterization data of dehydration product (5): R$_f$0.52 in 10% EtOAc/hex. UV active. Stains purple in anisaldehyde. Opt. Rot. α$_{obs}$=−289.5°, c=1.00 in CH$_2$Cl$_2$, T=22.3° C. $^1$H NMR (600 MHz, Chloroform-d) δ 5.84 (q, J=7.1 Hz, 1H), 5.69 (dd, J=10.1, 3.8 Hz, 1H), 5.66 (dd, J=10.3, 0.7 Hz, 1H), 4.88-4.84 (m, 1H), 4.76-4.72 (m, 1H), 3.72 (s, 3H), 3.08 (dd, =3.7, 0.7 Hz, 1H), 1.72 (d, J=7.1 Hz, 3H), 1.57-1.55 (m, 3H), 1.37 (s, 3H), 1.22 (s, 3H), 1.00 (s, 3H). $^{13}$C NMR (151 MHz, Chloroform-d) δ 214.5, 168.7, 144.5, 137.3, 131.5, 129.4, 129.0, 115.4, 57.7, 51.6, 50.5, 47.5, 27.6, 26.4, 22.8, 21.2, 15.5. HRMS Calculated C$_{17}$H$_{25}$O$_3$ [M+H] 277.1804|Found: 277.1810.

Example 4: Intramolecular Aldol Addition of 5 to Form 2

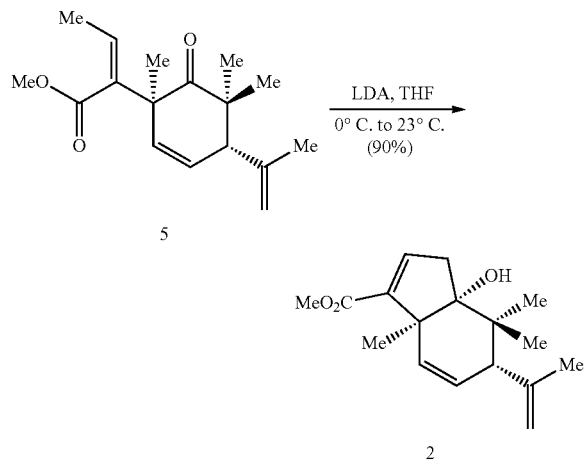

A [0.5M] solution of LDA in THF was made by addition of nBuLi ([2.67M in hex], 12.0 mmol, 4.5 mL) to a solution of HN$^i$Pr$_2$ (freshly distilled off CaH$_2$, 15.0 mmol, 2.10 mL) in anhydrous THF (17.4 mL) while cooled to −78° C. under an argon atmosphere. After addition of nBuLi, the solution was stirred at 0° C. for 20 minutes, then cooled back to −78° C.

A solution of substrate (>99% purity, 2.49 mmol, 687 mg) in anhydrous THF wider an argon atmosphere in a flame-dried 100 mL round bottom flask was cooled to 0° C. The LDA solution ([0.5M], 1.1 equiv., 5.5 mL) was added in a slow but steady stream via syringe to this solution at 0° C., which caused the solution to turn from clear and pale yellow to clear and orange/red. The solution stirred at 0° C. for 30 minutes, then warmed to 23° C. and monitored by TLC (20% EtOAc/hex, Anis.). Starting material still remained after 3 hours, so 100 μL more [0.5 M] LDA was added dropwise at 23° C. to this solution. TLC analysis indicated full consumption of starting material 1 hour after this (4 hours after the initial LDA addition).

The reaction was quenched by addition of NH$_4$Cl (aq., saturated, ~20 mL) and dilution with EtOAc (~20 mL). The reaction was extracted with EtOAc (3×~20 mL). The organic layer was dried over MgSO$_4$, filtered, and concentrated in vacuo. The crude mass (860 mg) was purified on silica gel (~250 mL) with 2 L of 10% EtOAc/hex. The desired compound was isolated as a yellow-white solid. (620 mg, 90% yield; see NOTE 1).

NOTE 1: The yield drops significantly if the substrate is impure. The excess LDA solution is maintained at −78° C. for the duration of the intramolecular aldol reaction. Use of a larger excess of LDA can lead to transposition of the α,β-unsaturated ester alkene and incorporation of molecular oxygen, so reaction monitoring by TLC and subsequent addition of small portions of LDA to drive the reaction to completion is preferable to use of more than 1.1 equivalents of LDA at the start of the reaction.

Characterization data of intramolecular aldol product (2): R$_f$ 0.52 in 10% EtOAc/hex. UV active and stains purple in anisaldehyde. Opt. Rot, α$_{obs}$=−27.6°, c=1.00 in CH$_2$Cl$_2$, T=21.0° C. $^1$H NMR (600 MHz, Chloroform-d) δ 6.67 (br dd, J=3.2, 2.0 1H), 5.98 (br d, J=10.3 Hz, 1H), 5.32 (br d, J=10.3 Hz, 1H), 5.02-4.99 (br m, 1H), 4.73 (hr s, 1H), 3.72 (s, 3H), 2.93 (br s, 1H), 2.92 (br d, J=18.5 Hz, 1H), 2.31 (dd, J=18.9, 3.2 Hz, 1H), 1.79 (s, 3H), 1.71 (br s, 1H), 1.42 (s, 3H), 1.06 (s, 3H), 1.00 (s, 3H). $^{13}$C NMR (151 MHz, Chloroform-d) δ 165.1, 145.8, 141.0, 140.6, 133.6, 126.7, 116.0, 85.4, 53.3, 52.1, 51.4, 42.6, 40.3, 24.0, 23.3, 18.8, 18.5. HRMS Calculated C$_{17}$H$_{25}$O$_3$ [M+H]: 277.1804|Found: 277.1810.

Example 5: Bromoetherification of 2 to Form 6

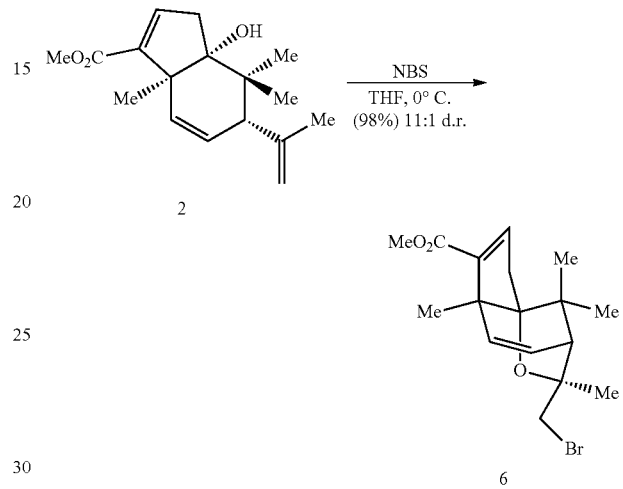

A flame-dried 50 mL round bottom flask was charged with solid triene substrate 2 (1.0 equiv, 610 mg, 2.21 mmol) and a stir bar and placed under an argon atmosphere at 0° C. in an ice-water bath. A separate flame-dried 50 mL round bottom flask was charged with NBS (recrystallized, 2.0 equiv, 4.42 mmol, 787 mg) and anhydrous THF ([0.2 M], wrt NBS) at 0° C. in an ice-water bath and kept out of light (wrapped in foil and hood light turned off). Without stirring (See NOTE 1), the NBS/THF solution was then transferred by cannula (see NOTE 2) with differential pressure under an Argon atmosphere at 0° C. The solution after transfer was clear and pale yellow. The reaction was stirred at 0° C. in the dark (fume hood lights off and the reaction flask was wrapped in foil) and monitored by TLC (15% EtOAc/hex, Anis.). No starting material remained after 2 hours.

The reaction was worked-up by addition to a mixture of NH$_4$Cl (saturated, aq., ~50 mL) and EtOAc (~50 mL). The aqueous layer was extracted with EtOAc (3×~100 mL) and then washed with NaHCO$_3$ (saturated, 1×~50 mL). The organic layer was dried over MgSO$_4$, filtered, and concentrated in vacuo. The crude mass (~1.2 g) was dry-loaded with celite onto a silica column (~100 mL of silica) and purified by flash column chromatography with 15% EtOAc/hex. The desired compound was isolated as a yellow-tinged white solid. (776 mg, 98% yield, 11:1 diastereoselectivity in favor of the endo diastereomer shown above). Isolated yields for this reaction ranged between 92-98% for different runs.

NOTE 1: Dissolution of the substrate in THF prior to addition of the NBS/THF solution diminishes the diastereoselectivity of the reaction. Although the diastereoselectivity of this step is technically inconsequential because the stereocenter is erased by the final zinc reduction step, low diastereoselectivity at this step complicates analysis and characterization of the products of subsequent steps.

NOTE 2: The cannula was cooled during transfer by contact with solid dry ice.

Characterization data of bromoetherification product (major diastereomer) (6): $R_f$ 0.37 in 10% EtOAc/hx. UV active and stains purple in anisaldehyde. Opt. Rot. $\alpha_{obs}$=−14.7°, c=1.00 in $CH_2Cl_2$, T=21.5° C. (on 11:1 diastereomeric mixture). $^1$H NMR (600 MHz, Chloroform-d) δ 6.53 (dd, J=3.5, 2.2 Hz, 1H), 6.25 (d, J=9.6 Hz, 1H), 5.97 (dd, J=9.6, 6.9 Hz, 1H), 3.72 (s, 3H), 3.66 (dd, J=9.2, 1.1 Hz, 1H), 3.40 (d, J=9.2 Hz, 1H), 2.59 (ddd, J=18.1, 2.2, 0.7 Hz, 1H), 2.46 (ddd, J=18.2, 3.6, 0.8 Hz, 1H), 2.21 (d, J=6.9 Hz, 1H), 1.65 (d, J=1.0 Hz, 3H), 1.29 (s, 3H), 1.23 (s, 3H), 0.98 (s, 3H). $^{13}$C NMR (151 MHz, Chloroform-d) δ 164.3, 142.7, 139.1, 132.7, 128.0, 95.9, 85.2, 52.9, 52.8, 51.4, 46.2, 42.9, 32.1, 27.2, 27.0, 26.2, 20.6. HRMS Calculated $C_{17}H_{24}BrO_3$ [M+H] 355.0909|Found: 355.0907.

Example 6: Enoxidation of 6 to Form 7

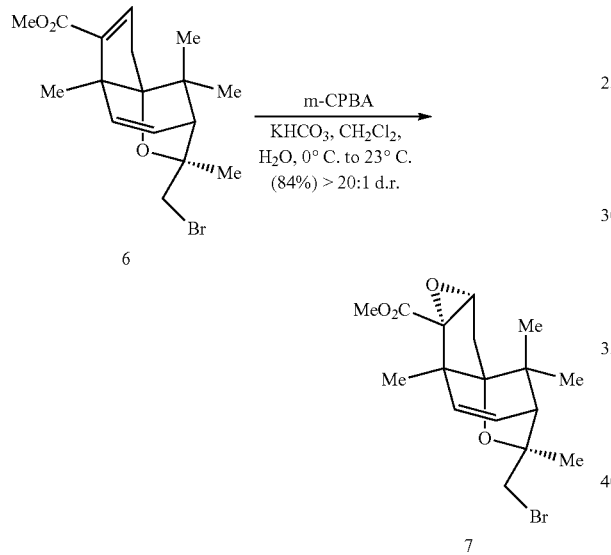

To a suspension of substrate 6 (2.5 g, 7.0 mmol, 1 equiv) in $CH_2Cl_2/H_2O$ (5:1, v:v, 120 mL) was added $KHCO_3$ (5.6 g, 56.0 mmol, 8 equiv.) and stirred vigorously for 15 min. The biphasic reaction mixture was then cooled to 0° C. and mCPBA (50% purity, 9.66 g, 28.0 mmol, 4 equiv) was slowly added portion-wise. The solution was stirred vigorously for 2 hours at room temperature, during which time a white precipitate formed. TLC indicated starting material consumption. The reaction was quenched by slowly adding a saturated $Na_2S_2O_3$ solution (aq., 20 mL) at 0° C., then diluted by $H_2O$ (100 mL) and $CH_2Cl_2$ (200 mL). The aqueous layer was extracted with $CH_2Cl_2$ (3×100 mL). The combined organics were dried over $Na_2SO_4$, filtered, and concentrated in vacuo. The crude product was purified by column chromatography over silica gel (5% EtOAc/Hexane) to afford epoxide 7 (2.18 g, 5.88 mmol, 84%) as a single diastereomer.

Characterization data of epoxidation product (7): $R_f$ 0.28 in 10% EtOAc/hex. Stains purple in anisaldehyde. Opt. Rot. $\alpha_{obs}$=−36.0°, c=1.00 in $CH_2Cl_2$, T=22.0° C. $^1$H NMR (600 MHz, Chloroform-d) δ 6.20 (dd, J=9.6, 0.7 Hz, 1H), 6.02 (dd, J=9.6, 6.9 Hz, 1H), 3.75 (dd, J=4.1, 1.0 Hz, 1H), 3.71 (s, 3H), 3.60 (dd, J=9.2, 1.1 Hz, 1H), 3.31 (d, J=9.2 Hz, 1H), 2.23 (d, J=6.9 Hz, 1H), 2.12 (ddd, J=14.6, 4.2, 0.9 Hz, 1H), 1.84 (dt, J=14.6, 1.0 Hz, 1H), 1.61 (d, J=1.1 Hz, 3H), 1.29 (s, 4H), 1.16 (s, 3H), 1.14 (s, 3H). $^{13}$C NMR (151 MHz, Chloroform-d) δ 168.1, 133.1, 127.6, 99.4, 85.9, 66.0, 61.5, 52.5, 52.0 (observed by HSQC), 48.2, 46.6, 42.6, 29.3, 28.1, 26.2, 24.2, 17.1. HRMS Calculated $C_{17}H_{24}BrO_4$ [M+H]: 371.0858|Found: 371.0856.

Example 7: Dihydroxylation of 7 to Form 8

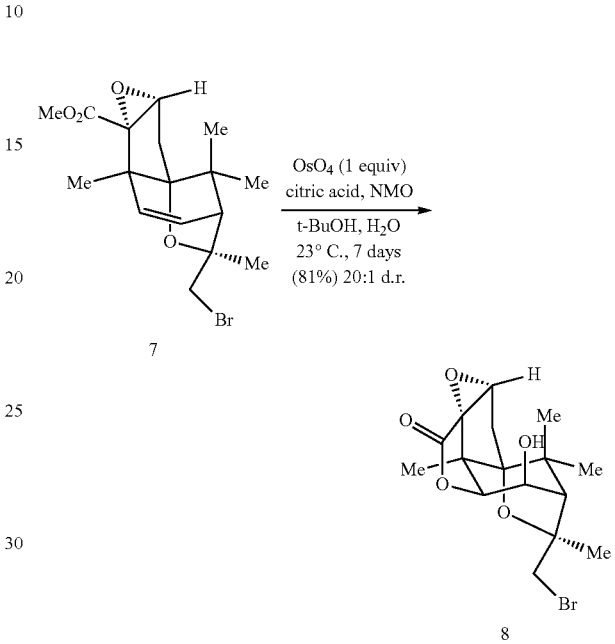

A 1 L round bottom flask was charged with a magnetic stir bar, the alkene substrate 7 (3.31 g, 8.92 mmol, 1 equiv), citric acid (3.43 g, 17.84 mmol, 2 equiv), NMO (3.13 g, 26.76 mmol, 3 equiv), and t-BuOH (57 mL). During this time, the fume hood lights were turned off and the reaction was wrapped with aluminum foil to minimize exposure to ambient light. $OsO_4$ (57 mL, 4 wt % in $H_2O$, 9.37 mmol, 1.05 equiv, NOTE 1) was then added at room temperature in the dark. The reaction was capped with a yellow cap (a 24/40 polyethylene flask stopper), sealed with duct tape, and stirred vigorously (>1000 rpm) for 7 days at room temperature. During the course of the reaction, the yellow cap was stained black by osmium tetroxide. The reaction was quenched by adding a saturated solution of $Na_2S_2O_3$ (20 mL) after cooling the reaction to 0° C. After stirring for 15 min, the dark yellow solution changed to black suspension, hood lamps were turned on, the reaction mixture was diluted with EtOAc (200 mL), then extracted with EtOAc (3×300 mL). The combined organic layer was dried over $Na_2SO_4$, filtered, and concentrated in vacuo. The crude mixture was purified by column chromatography over silica gel (30% EtOAc/Hexane to 50% EtOAc/Hexane) to afford desired dihydroxylation product 8 (2.7 g, 7.23 mmol, 81%, 89% brsm) as single diastereoisomer. Starting material 7 (298 mg, 0.8 mmol, 9%) was recovered.

NOTE 1: $OsO_4$ 4 wt % in $H_2O$ is a commercially available greenish solution. It may also be made from $OsO_4$ solid in deionized $H_2O$. $OsO_4$ is a highly toxic volatile solid so use of an efficient fume hood is strongly recommended for this procedure.

Characterization data of dihydroxylation product (8): $R_f$ 0.41 in 50% EtOAc/Hex. Anis. Stains dark blue/purple.

Opt. Rot. α$_{obs}$=2.4°, c=1.00 in CH$_2$Cl$_2$, T=20.7° C. $^1$H NMR (600 MHz, Chloroform-d) δ 4.78 (d, J=8.8 Hz, 1H), 4.70 (ddd, J=8.9, 3.5, 1.5 Hz, 1H), 3.89 (dd, J=3.9, 1.6 Hz, 1H), 3.35 (d, J=10.4 Hz, 1H), 3.28 (d, J=10.4 Hz, 1H), 2.23 (dd, J=14.6, 3.9 Hz), 2.24-2.21 (m, 2H), 1.96 (ddd, J=14.6, 1.6, 0.9 Hz, 1H), 1.65 (s, 3H), 1.31 (s, 3H), 1.25 (s, 3H), 1.23 (s, 3H). $^{13}$C NMR (151 MHz, Chloroform-d) δ 170.7, 100.6, 82.4, 79.4, 68.4, 67.7, 63.1, 56.9, 44.3, 44.1, 40.9, 31.8, 29.8, 27.5, 22.7, 18.7. HRMS (M+H) Calculated C$_{16}$H$_{22}$BrO$_5$ [M+H]: 373.0651|Found: 373.0646.

Opt. Rot. α$_{obs}$=-17.0°, c=0.50 in CH$_2$Cl$_2$, T=20.0° C. $^1$H NMR (600 MHz, Chloroform-d) 5.22 (t, J=5.3 Hz, 1H), 4.76 (d, J=5.2 Hz, 1H), 3.96 (dd, J=3.6, 1.5 Hz, 1H), 3.52 (dd, J=10.6, 1.2 Hz, 1H), 3.41 (d, J=10.7 Hz, 1H), 3.16 (dd, J=5.5, 0.9 Hz, 1H), 2.46 (dd, J=14.4, 3.6 Hz, 1H), 1.94 (dt, J=14.4, 1.3 Hz, 1H), 1.61 (d, J=1.0 Hz, 3H), 1.56 (s, 3H), 1.36 (s, 3H), $^{13}$C NMR (151 MHz, Chloroform-d) δ 173.6, 168.3, 97.3, 84.2, 78.3, 75.8, 67.7, 63.3, 60.5, 53.9, 47.8, 36.8, 33.9, 26.5, 19.7, 17.4. HRMS Calculated C$_{16}$H$_{18}$BrO$_6$ [M+H]: 385.0287|Found: 385.0279.

Example 8: Oxidation of 8 to 18

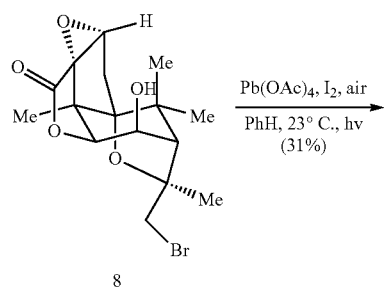

Example 9: Reductive Debromination of 18 to Form 5-Methyl-Picrotoxinin (20)

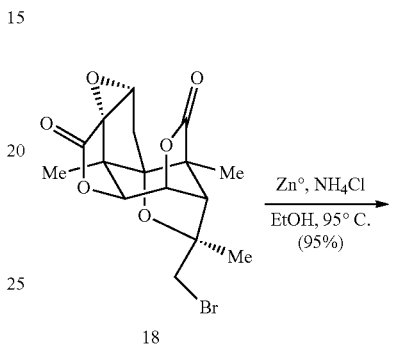

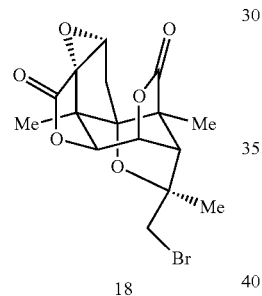

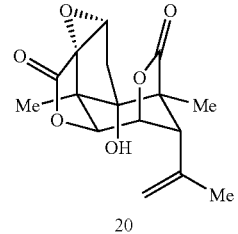

To a solution of Pb(OAc)$_4$ (592 mg, 1.34 mmol, 5 equiv, NOTE 1) in benzene (10 mL) was added 12 (340 mg, 1.34 mmol, 5 equiv) in the dark (covered with aluminum foil and hood light turned-off) at room temperature and stirred for 30 min. To a suspension of 8 (100 mg, 0.27 mmol, 1 equiv) and CaCO$_3$ (270 mg, 2.7 mmol, 10 equiv) in benzene (5 mL) was added the Pb(OAc)$_4$/I$_2$/benzene solution at room temperature. The hood lamps were turned on and the reaction was vigorously stirred at room temperature under ambient light for 2.5 h. Consumption of 8 was monitored by TLC. The reaction was quenched by saturated Na2S2O3 (5 mL) at 0° C. then filtered through a short pad of Celite, washed with EtOAc (3×10 mL). The combined organic layer was dried over Na$_2$SO$_4$, filtered, and concentrated in vacuo. The crude product was purified by column chromatography over silica gel (50% EtOAc/Hexane) to afford 5-methyl-bromopicrotoxinin 18 (32 mg, 0.084 mmol, 31%) as a white solid.

NOTE 1: Commercially available Pb(OAc)$_4$ is stabilized with AcOH, pure Pb(OAc)$_4$ could be freshly recrystallized from AcOH, then washed three times with hexane prior to use.

Characterization data of oxidation product (18): R$_f$ 0.51 in 50% EtOAc/hex. Stains weakly grey/green in anisaldehyde.

Zinc powder (55 mg, 0.84 mmol, 10 equiv), NH$_4$Cl (90 mg, 1.68 mmol, 20 equiv) were added into a solution of 5-methyl-bromopicrotoxinin 18 (32 mg, 0.084 mmol, 1 equiv) in EtOH/H$_2$O (v:v, 10:1, 6.6 mL). Then the reaction was warmed up to 95° C. and stirred at this temperature for 2 h. The reaction mixture was diluted by EtOAc (5 mL) then filtered through a short pad of Celite and washed with EtOAc (3×3 mL). The reaction mixture was concentrated and purified by column chromatography over silica gel (10% EtOAc/CH$_2$Cl$_2$) to give 5-methyl-picrotoxinin 20 (24.4 mg, 0.08 mmol, 95%) as a white solid.

Characterization data of 5-methyl-picrotoxinin (20): Rf 0.31 in 40% EtOAc/hex. Stains brown in anisaldehyde. Opt. Rot, α$_{obs}$=-1.2°, c=0.10 in CH$_2$Cl$_2$, T=20.0° C. $^1$H NMR (600 MHz, Chloroform-d) δ 5.11 (p, J=1.6 Hz, 1H), 5.05 (d, J=2.1 Hz, 1H), 5.02 (dd, J=5.2, 3.4 Hz, 1H), 4.83 (d, J=3.4 Hz, 1H), 3.70 (dd, J=3.6, 0.7 Hz, 1H), 3.14 (d, J=5.1 Hz, 1H), 2.97 (dd, J=15.3, 3.6 Hz, 1H), 1.96 (dt, J=1.6, 0.9 Hz, 3H), 1.88 (s, 1H), 1.75 (d, J=15.3 Hz; 1H), 1.53 (s, 3H), 1.26 (s, 3H). $^{13}$C NMR (151 MHz, Chloroform-d) δ 177.2, 168.9, 139.4, 115.6, 88.7, 80.2, 76.1, 72.6, 62.0, 53.9, 51.0, 47.4, 42.5, 24.3, 17.1, 17.0. HRMS Calculated C$_{16}$H$_{19}$O$_6$ [M+H]: 307.1182|Found: 307.1178.

Example 10: Etherification of 8 to Form 9

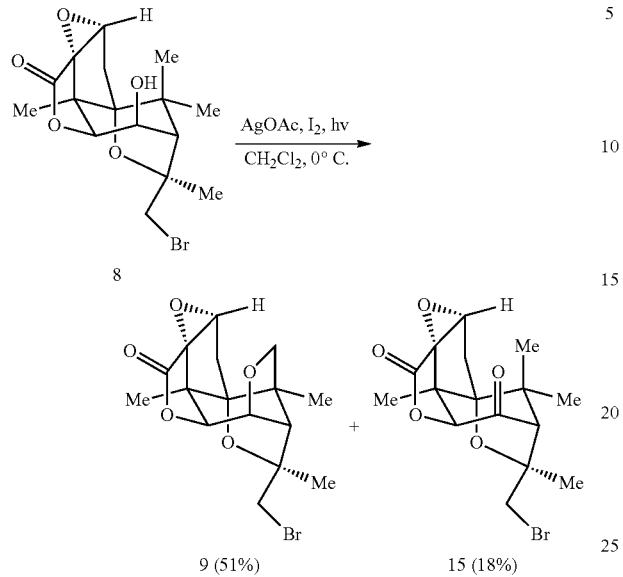

Example 11: TFDO Oxidation of 9 to Form 10

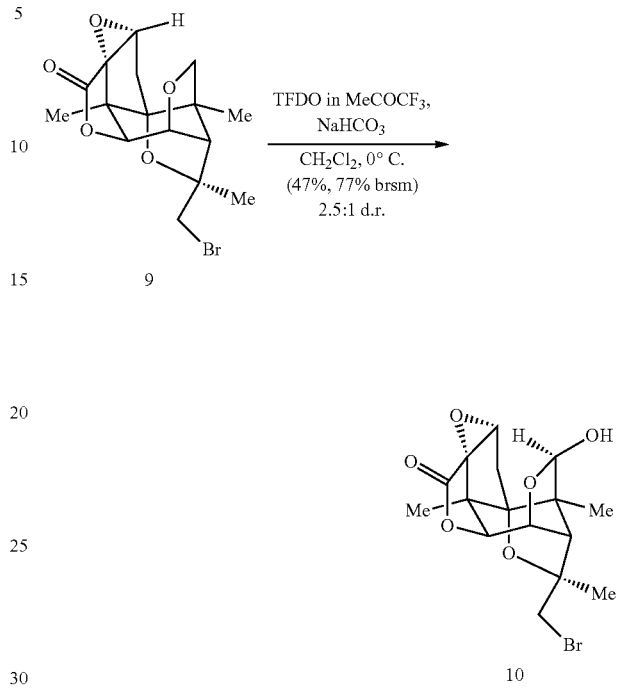

Two reactions were carried out in parallel. To a suspension of alcohol 8 (2×(50 mg, 0.13 mmol, 1 equiv)) and AgOAc (2×(109 mg, 0.65 mmol, 5 equiv)) in $CH_2Cl_2$ (2×5 mL) was added $I_2$ (2×(165 mg, 0.65 mmol, 5 equiv) as solid at 0° C. The reaction was vigorously stirred under ambient light for 1 hour, then quenched with saturated $Na_2S_2O_3$ (aq., 0.5 mL each) at 0° C. The two reactions were combined, filtered through a short pad of celite and washed with $CH_2Cl_2$ (3×10 mL). The crude product was concentrated in vacuo and then purified by column chromatography over silica gel (5% $EtOAc/CH_2Cl_2$ to 10% $EtOAc/CH_2Cl_2$) to give ether 9 (49 mg, 0.13 mmol, 51%) as colorless foam and the major byproduct, ketone 15 (17 mg, 0.047 mmol, 18%), as pale yellow solid.

Characterization data of ether 9: $R_f$ 0.51 in 10% $EtOAc/CH_2Cl_2$. Stains dark blue in anisaldehyde. Opt. Rot. $\alpha_{obs}$=−64.3°, c=2.00 in $CH_2Cl_2$, T=20.0° C. $^1H$ NMR (600 MHz, $CDCl_3$) δ 4.75 (dd, J=5.8 Hz, J=4.9 Hz, 1H), 4.63 (d, J=5.8 Hz, 1H), 4.02 (d, J=11.1 Hz, 1H), 3.93 (dd, J=3.8, 1.5 Hz, 1H), 3.71 (d, J=11.1 Hz, 0.14), 3.42 (d, J=10.7 Hz, 3.34 (d, J=107 Hz, 1H), 2.68 (d, J=4.9 Hz, 2.32 (dd, J=14.6, 3.8 Hz, 1H), 1.99 (d, J=14.6 Hz, 1H), 1.59 (s, 3H), 1.38 (s, 3H), 1.31 (s, 3H). $^{13}C$ NMR (150 MHz, $CDCl_3$) δ 169.8, 100.1, 81.8, 81.6, 77.0 (overlaps with $CDCl_3$), 71.8, 69.0, 62.4, 60.6, 54.7, 46.1, 38.7, 33.5, 26.7, 21.6, 18.1. HRMS Calculated $C_{16}H_{20}BrO_5[M+H]$: 371.0494|Found: 371.0489.

Characterization data of ketone 15: $R_f$ 0.57 in 5% $EtOAc/CH_2Cl_2$. Stains blue in anisaldehyde. Opt. Rot. $\alpha_{obs}$=−43.0°, c=0.50 in $CH_2Cl_2$, T=20.0° C. $^1H$ NMR (600 MHz, $CDCl_3$) δ 4.51 (s, 1H), 3.94 (dd, J=3.8, 1.6 Hz, 1H), 3.27 (d, J=11.0 Hz, 1H), 3.22 (d, 11.0 Hz, 1H), 2.84 (s, 1H), 2.34 (dd, J=14.7, 3.8 Hz, 1H), 2.12 (ddd, J=14.7, 1.6, 0.9 Hz, 1H), 1.62 (s, 3H), 1.41 (s, 3H), 1.38 (s, 3H), 1.13 (s, 3H). $^{13}C$ NMR (150 MHz, $CDCl_3$) δ 202.3, 169.4, 100.6, 82.8, 81.6, 69.4, 68.1, 63.0, 47.6, 45.2, 39.3, 32.1, 28.7, 26.8, 21.7, 18.1. HRMS Calculated $C1_{16}H_{20}BrO_5$ [M+H]: 371.0494|Found: 371.0491.

To a 20 mL vial was charged ether 9 (60 mg, 0.16 mmol, 1 equiv) and $NaHCO_3$ (59 mg, 0.7 mmol, 4.4 equiv) in $CH_2Cl_2$ (1.5 mL). During this time, the flume hood lights were turned off and the reaction was wrapped with aluminum foil to minimize exposure to ambient light. A TFDO solution (~0.5 M in 1,1,1-trifluoroacetone, 3 mL, 1.5 mmol, 9.4 equiv, NOTE 1) was added dropwise at 0° C. The reaction was vigorously stirred for 6 h in the dark, then quenched with saturated $Na_2S_2O_3$ (0.5 mL) at 0° C. The mixture was warmed up slowly to room temperature and filtered through a short pad of Celite and washed with C1-2C12 (2×10 mL). The crude product was concentrated in vacuo and then purified by column chromatography over silica gel (10% $EtOAc/CH_2Cl_2$ to 30% $EtOAc/CH_2Cl_2$). The desired lactol 10 (29 mg, 0.075 mmol, 47%, 77% brsm was obtained as a colorless oil diastereomer mixture (dr~2.5:1), 9 (23.8 mg, 0.064 mmol, 40%) was recovered (NOTE 2).

NOTE 1: A methyl(trifluoromethyl)dioxirane (TFDO) solution in trifluoroacetone was prepared according to *Tetrahedron* 1996, 52, 2377-2384 or Baran's TFDO Synthesis Procedure (http://openflask.blogspot.com/2014/01/tfdo-synthesis-procedure.html). The TFDO solution should be titrated before use. A 0.1 mL TFDO solution was added into the mixture of 0.5 mL $H_2O$, 1.5 mL AcOH and 0.25 mL saturated KI at −78° C. This dark red solution was then titrated with 0.05 M $Na_2S_2O_2$ at room temperature.

NOTE 2: The endo lactol epimer of 10 was observed to irreversibly decompose via intramolecular epoxide opening (endo-10 to SI-2) during storage either neat or as solution in $CH_2Cl_2$ in a−20° C. freezer. The less polar SI-2 could be isolated as a white solid. Due to decomposition, using lactol 10 directly with minimal storage time is strongly recommended.

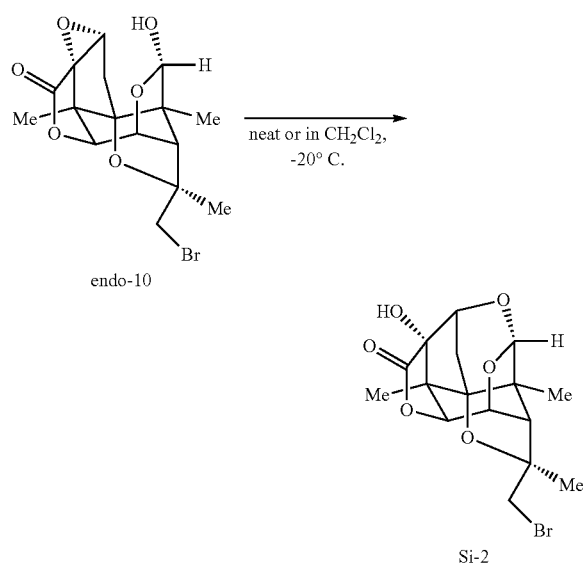

Characterization data of lactol 10 (major diastereomer): $R_f$ 0.37 in 30% EtOAc/$CH_2Cl_2$. Stains red purple in anisaldehyde. Opt. Rot. $\alpha_{obs}$=−42.5°, c=1.00 its $CH_2Cl_2$, T=20.0° C. $^1$H NMR (600 MHz, $CDCl_3$) δ 5.33 (s, 1H), 4.88 (dd, J=5.4 Hz, J=5.2 Hz 1H), 4.61 (d, J=5.4 Hz, 1H), 4.11 (dd, J=3.8, 1.5 Hz, 1H), 3.44 (d, J=11.2 Hz, 1H), 3.35 (d, J=10.6 Hz, 1H), 2.91 (d, J=5.2 Hz, 1H), 2.47 (dd, J=14.6, 3.8 Hz, 1H), 1.96 (d, J=14.6 Hz, 1H), 1.58 (s, 3H), 1.38 (s, 3H), 1.29 (s, 3H). $^{13}$C NMR (150 MHz, $CDCl_3$) δ 170.4, 98.7, 96.7, 82.7, 81.0, 76.6, 68.4, 62.4, 59.1, 57.6, 46.6, 38.6, 33.6, 26.5, 19.4, 17.8. HRMS Calculated $C_{16}H_{20}BrO_6$ [M+H]: 387.0443|Found: 387.0439.

Example 12: Fragmentation of 10 to Form 11

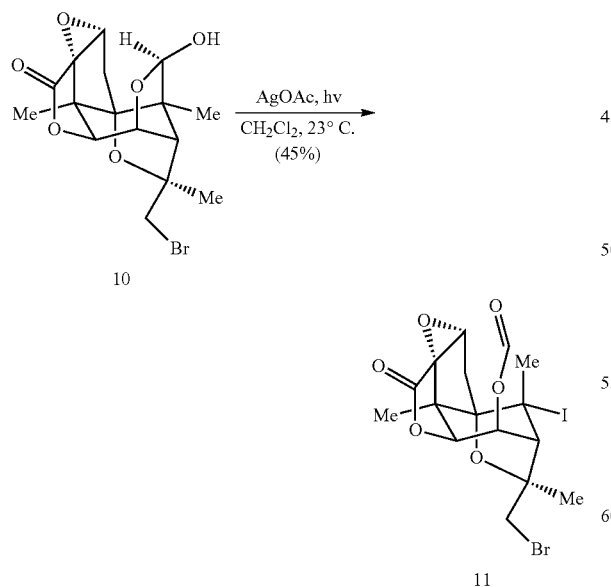

A 25 mL screw cap test tube was charged with a solution of lactol 10 (20 mg, 0.052 mmol, 1 equiv) in $CH_2Cl_2$ (3 mL), AgOAc (52 mg, 0.31 mmol, 6 equiv) and 12 (79 mg, 0.31 mmol, 6 equiv) in the dark. (The hood lights were kept off during this process and the reaction was wrapped with aluminum foil). After stirring for 10 min in the dark, the hood lamps were turned on, and the reaction was vigorously stirred at room temperature under ambient light for 1 hour. The reaction was monitored by TLC for consumption of starting material. The reaction was quenched by saturated $Na_2S_2O_3$ (0.5 then filtered through a short pad of Celite, washed with $CH_2Cl_2$ (3×5 and concentrated in vacuo. The crude product was purified by column chromatography over silica gel (15% EtOAc/Hexane) to afford iodide formate 11 (12 mg, 0.023 mmol, 45%) as a colorless oil.

NOTE: Due to the sensitivity of iodide formate 11 to light, storage of this compound in a $CH_2Cl_2$ solution covered with aluminum foil in the −20° C. freezer is recommended.

Characterization data of iodide 11: $R_f$ 0.63 in 33% EtOAc/Hexane. Stains brown in anisaldehyde. Opt. Rot. $\alpha_{obs}$=+24.0°, c=0.40 in $CHCl_3$, T=20.0° C. $^1$H NMR (600 MHz, $CDCl_3$) δ 8.09 (d, J=1.1 Hz, 1H), 5.55 (d, J=8.7 Hz, 1H), 4.95 (d, J=8.7 Hz, 1H), 4.01 (dd, J=3.9, 1.6 Hz, 1H), 3.44 (d, J=10.6 Hz, 1H), 3.36 (d, J=10.6 Hz, 1H), 2.99 (d, J=1.4 Hz, 1H), 2.81 (dd, J=15.1, 4.0 Hz, 1H), 2.59 (s, 3H), 2.22-2.14 (m, 4H), 1.35 (s, 3H). $^{13}$C NMR (150 MHz, $CDCl_3$) δ 169.7, 159.0, 102.8, 83.8, 76.5, 68.7, 68.1, 62.8, 60.5, 58.9, 44.1, 40.2, 39.7, 32.6, 28.9, 20.0. HRMS Calculated $C_{16}H_{19}BrIO_6$ [M+H]: 512.9410|Found: 512.9401.

Example 13: Reductive Deiodination and Deformylation of 11 to 12

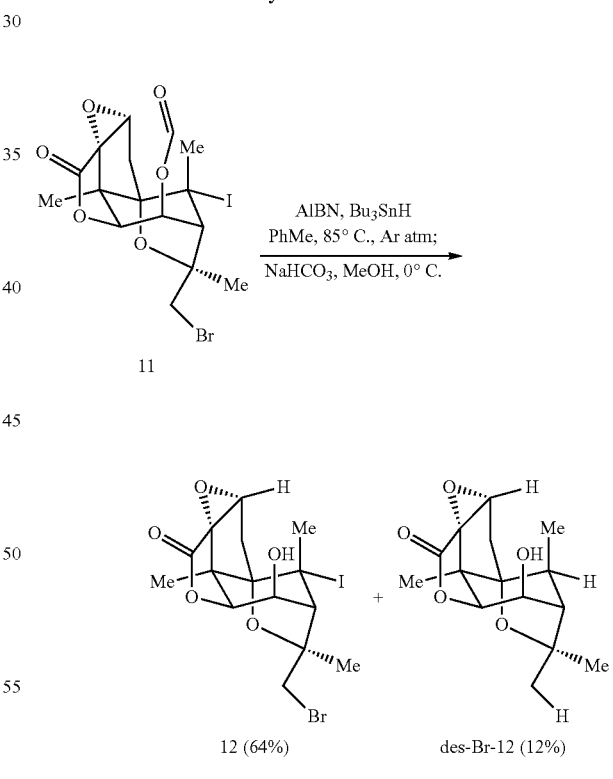

To a 10 mL microwave tube were added a solution of iodide formate 11 (24 mg, 0.047 mmol, 1 equiv) in toluene ml freshly distilled over sodium and benzophenone), AIBN (3.8 mg, 0.023 mmol, 0.5 equiv) and $nBu_3SnH$ (1.6 μL, 0.061 mmol, 1.3 equiv) in the dark. The reaction mixture was then degassed using 5 freeze-pump-thaw cycles. (Each freeze-pump-thaw cycle was conducted as described: the reaction mixture was frozen in liquid $N_2$ for 10 min, then evacuated under high vacuum and backfilled with argon gas three times. The mixture was then warmed up to room temperature to melt the solid.) The reaction mixture was heated at 85° C. for 30 min and consumption of starting material was monitored by TLC. Upon completion, the solvent was removed under high vacuum to give a pale-yellow residue. The residue was cooled to 0° C., then methanol (4 mL) and a saturated $NaHCO_3$ (0.2 mL) solution were added. After stirring at 0° C. for 1 h, reaction was concentrated in vacuo. The crude product was purified by silica gel chromatography (50% EtOAc/Hexane) to afford 12 (10.8 mg, 0.03 mmol, 64%) as a colorless oil and des-Br-12 (1.5 mg, 0.006 mmol, 12%) as a white solid.

NOTE 1: To minimize decomposition of ambient light-sensitive iodide formate 11, all manipulations of this reaction should be conducted with minimal exposure to light. The hood lights were kept off during this process and the reaction was wrapped with aluminum foil.

NOTE 2: Five freeze-pump-thaw cycles were found to be necessary for efficient reduction of the tertiary iodide 11. Less thorough degassing procedures allow for oxygen incorporation at C5.

Characterization data of 12: $R_f$ 0.56 in 50% EtOAc/Hexane. Stains purple in anisaldehyde. Opt. Rot. $\alpha_{obs}$=−3.2°, c=0.25 in $CHCl_3$, T=20.0° C. $^1$H NMR (600 MHz, $CDCl_3$) δ 4.77 (d, J=8.5 Hz, 1H), 4.64 (d, J=8.4 Hz, 1H), 3.87 (dd, J=3.8, 1.5 Hz, 1H), 3.36 (d, J=10.4 Hz, 1H), 3.20 (d, J=10.4 Hz, 1H), 2.46-2.38 (m, 1H), 2.33 (d, J=3.9 Hz, 1H), 2.16 (d, J=14.3 Hz, 1H), 2.06 (dd, J=14.3, 3.8 Hz, 1H), 1.49 (s, 3H), 1.24 (d, J=8.0 Hz, 3H), 1.13 (s, 3H). $^{13}$C NMR (150 MHz, $CDCl_3$) δ 170.4, 97.2, 83.0, 78.8, 68.2, 66.2, 62.3, 51.4, 42.3, 42.1, 37.4, 35.9, 27.1, 17.8, 11.9. HRMS Calculated $C_{15}H_{20}BrO_5$[M+H]: 359.0494|Found: 359.0497.

Characterization data of des-Br-12: $R_f$ 0.32 in 50% EtOAc/Hexane. Stains pimple in anisaldehyde. Opt. Rot. $\alpha_{obs}$=+22.9°, c=0.14 in MeOH, T=20.0° C. $^1$H NMR (600 MHz, $CDCl_3$) δ 4.75 (d, J=8.5 Hz, 1H), 4.52 (d, J=8.5 Hz, 1H), 3.86 (dd, J=3.8, 1.4 Hz, 1H), 2.36 (ddd, J=7.9, 4.0, 1.4 Hz, 1H), 2.13 (t, J=7.5 Hz, 2H), 2.08-2.00 (m, 1H), 1.30 (s, 3H), 1.27 (s, 3H), 1.22 (d, J=8.0 Hz, 3H), 1.14 (s, 3H). $^{13}$C NMR (150 MHz, $CDCl_3$) δ 170.8, 96.6, 81.7, 79.1, 68.3, 67.3, 62.6, 52.4, 42.4, 42.1, 35.9, 30.9, 25.9, 17.8, 12.0. HRMS Calculated $C_{15}H_{21}O_5$ [M+H]: 281.1389|Found: 281.1383.

Example 14: Oxidation of 12 to Bromopicrotoxinin (SI-3)

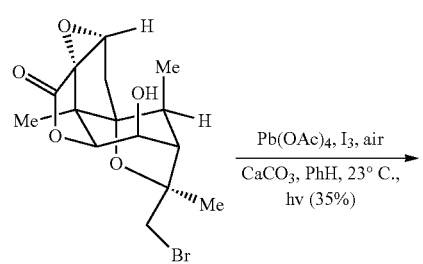

12

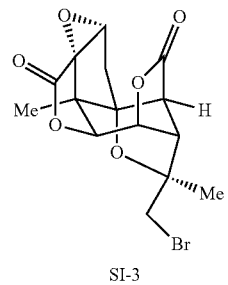

SI-3

To a solution of $Pb(OAc)_4$ (53 mg, 0.12 mmol, 5 equiv, freshly recrystallized from AcOH, then washed three times with hexane) in benzene (2 mL) was added 12 (30 mg, 0.12 mmol, 5 equiv) in the dark (covered with aluminum foil and hood light turned off) at room temperature and stirred for 30 min. To a suspension of 12 (8.6 mg, 0.024 mmol, 1 equiv), $CaCO_3$ (24 mg, 0.24 mmol, 10 equiv) in benzene (1 was added the $Pb(OAc)_4/I_2$/PhH solution at room temperature under ambient atmosphere. The hood lamps were turned on, and the reaction was vigorously stirred at room temperature under ambient light for 2.5 hours. Consumption of starting material was monitored by TLC. The reaction was quenched with saturated $Na_2S_2O_3$ (0.5 mL) then filtered through a short pad of celite, washed with EtOAc (3×5 mL), and concentrated in vacuo. The crude product was purified by prep thin layer chromatography (50% 1361.2861.51 EtOAc/Hexane) to afford bromopicrotoxinin SI-3 (3.1 mg, 0.008 mmol, 35%) as a white solid.

Characterization data of SI-3: $R_f$ 0.53 in 50% EtOAc/Hexane. Stains brown in anisaldehyde. Opt. Rot. $\alpha_{obs}$=−123.6°, c=0.28 in $CH_2Cl_2$, T=20.0° C. [cf. *JACS* 1989, 111, 3728: $[\alpha]^{27}{}_D$:=−126° (c=0.21, $CHCl_3$)]. $^1$H NMR (600 MHz, $CDCl_3$) δ 5.23 (td, J=5.2, 1.0 Hz, 1H), 4.71 (d, J=5.1 Hz, 1H), 4.06 (dd, J=3.6, 1.2 Hz, 1H), 3.51-3.40 (m, 3H), 3.06 (dd, J=5.3, 0.8 Hz, 1H), 2.45 (dd, J=14.0, 3.6 Hz, 1H), 2.27-2.19 (m, 1H), 1.56 (s, 3H), 1.33 (s, 3H). $^{13}$C NMR (150 MHz, $CDCl_3$) δ 170.3, 168.1, 94.7, 85.0, 77.63, 77.59, 67.7, 63.3, 55.7, 54.2, 47.2, 38.4, 35.4, 27.9, 16.9. HRMS Calculated $C_{15}H_{16}BrO_6$ [M+H]: 371.0130|Found: 371.0128.

Example 15: Reductive Debromination of Bromopicrotoxinin (SI-3) to Form Picrotoxinin (1)

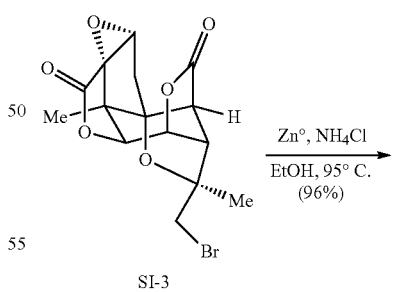

SI-3

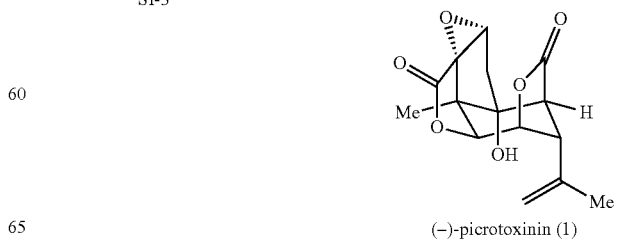

(−)-picrotoxinin (1)

Zinc powder (10 mg, 0.15 mmol, 10 equiv), NH$_4$Cl (16 mg, 0.3 mmol, 20 equiv) were added into a solution of bromopicrotoxinin (SI-3) (5.3 mg, 0.015 mmol, 1 equiv) in EtOH/H$_2$O (v:v, 10:1, 2.2 mL). Then the reaction was warmed up to 95° C. and stirred at this temperature for 2 hours. The reaction mixture was diluted by EtOAc then filtered through a short pad of Celite and washed with EtOAc (3×2 mL). The reaction mixture was concentrated and purified by prep thin layer chromatography (10% EtOAc/CH$_2$Cl$_2$) to give picrotoxinin (1) (4.2 mg, 0.014 mmol, 96%) as a white solid.

Characterization data of picrotoxinin (1): R$_f$0.38 in 10% EtOAc/CH$_2$Cl$_2$. Stains dark blue in anisaldehyde. Opt. Rot. $\alpha_{obs}=-95°$, c=0.20 in CHCl$_3$, T=20.0° C. [cf. JACS 1984, 106, 4547: $[\alpha]^{27}_D=-6.7°$ (c=1.03, CHCl$_3$)]. $^1$H NMR (600 MHz, CDCl$_3$) δ 5.17-5.01 (m, 2H), 4.89 (d, J=3.6 Hz, 1H), 4.85 (d, J=1.9 Hz, 1H), 3.74 (d, J=3.0 Hz, 1H), 3.44 (s, 1H), 2.97 (dd, J=15.1, 3.6 Hz, 2H), 1.99 (d, J=15.1 Hz, 1H), 1.96-1.89 (m, 3H), 1.25 (s, 3H). $^{13}$C NMR (150 MHz, CDCl$_3$) δ 173.8, 168.7, 139.8, 113.6, 86.3, 79.6, 77.2, 72.4, 61.6, 50.8, 48.7, 46.7, 44.7, 23.3, 16.6. HRMS Calculated: C15H$_{17}$O$_6$ [M+H]: 293.1025|Found: 293.1029.

Example 16: Mukaiyama Hydration of Picrotoxinin (1) to Form Picrotin (19)

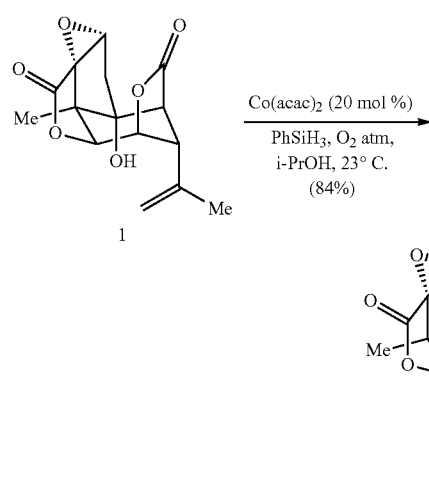

To a solution of 1 (18 mg, 0.062 mmol, 1 equiv) in iPrOH (0.4 mL) was added Co(acac)$_2$ (1.7 mg, 0.0068 mmol, 0.11 equiv) and PhSiH$_3$ (7.4 mg, 0.068 mmol, 1.1 equiv). The reaction was fitted with a balloon of O$_2$ and purged with sonication for 5 min. The reaction was stirred at room temperature for 2 hours at which time TLC analysis showed consumption of starting material. The reaction mixture was concentrated and purified by silica column chromatography to give picrotin (19) (16 mg, 84%) as a white solid.

Characterization data of picrotin (19): R$_f$0.16 in 20% EtOAc/Hexane. Stains dark blue in anisaldehyde. Opt. Rot. $\alpha_{obs}=-43.3°$, c=0.24 in EtOH, T=20.0° C. (cf. JACS 1989, 111, 3728: $[\alpha]^{25}_D=-69.9°$ (c=1.07, EtOH)). $^1$H NMR (600 MHz, Acetone-d) δ 5.91 (d, J=3.5 Hz, 5.58 (d, J=1.3 Hz 1H), 5.18 (ddd, J=5.1, 3.4, 0.7 Hz, 1H), 4.98 (d, J=3.4 Hz, 1H), 3.69 (d, J=3.3 Hz, 1H), 3.06 (ddd, J=5.2, 3.9, 1.1 Hz, 1H), 2.99-2.93 (m, 3H), 2.88 (ddd, J=14.9, 3.6, 2.0 Hz, 1H), 2.13 (d, J=14.3 Hz, 3H), 1.61 (s, 3H), 1.57 (s, 3H), 1.31 (s, 3H). $^{13}$C NMR (150 MHz, Acetone-d) δ 175.2, 170.1, 85.9, 81.3, 78.5, 74.1, 69.7, 62.3, 53.2, 51.3, 48.7, 44.0, 30.0, 28.8, 16.4. (cf. Phytochem. Anal. 2001, 12, 69. references the $^1$H NMR spectrum to 2.15 ppm, $^{13}$C NMR spectrum 206.15 ppm). HRMS Calculated: C$_{15}$H$_{19}$O$_7$[M+H]: 311.1131|Found: 311.1134.

Example 17: Hydrolytic Stability Study of Picrotoxin (1) Vs (20)

In separate 5 mm NMR tubes, picrotoxinin (1, 1 mg) or 5-methyl picrotoxinin (20, 1 mg) were dissolved in 1 mL of 100 mM phosphate buffer (pH=8, prepared with D20). Spectra were acquired at 0, 6, 12, 24, 36, 48, 60, 72, 84, 96, and 120 h. and monitored for the amount of hydrolysis product (Table 1).

TABLE 1

| | Concentrations of PXN (compound 1) and 5MePXN (compound 20) over Time | | | |
|---|---|---|---|---|
| Time (h) | [PXN] (mM) | ln [PXN] | [5MePXN] (mM) | ln [5MePXN] |
| 0 | 3.42 | 1.229640551 | 3.27 | 1.184789985 |
| 6 | 3.25714286 | 1.180850387 | 3 | 1.098612289 |
| 12 | 2.97391304 | 1.089878609 | 2.771186441 | 1.019275546 |
| 24 | 2.1242236 | 0.753406372 | 2.440298507 | 0.892120371 |
| 36 | 1.87912088 | 0.63080405 | 2.194630872 | 0.786013865 |
| 48 | 1.41322314 | 0.345873011 | 2.031055901 | 0.708555806 |
| 60 | 1.28089888 | 0.247562079 | 1.912280702 | 0.648296614 |
| 72 | 1.16723549 | 0.154638128 | 1.796703297 | 0.585953484 |
| 84 | 0.9144385 | −0.08944506 | 1.68556701 | 0.522102012 |
| 96 | 0.7755102 | −0.254234138 | 1.64321608 | 0.496655346 |
| 120 | 0.52941176 | −0.635988767 | 1.535211268 | 0.428668005 |

Example 18: Measurement of IC$_{50}$ Value for 5-Methyl-Picrotoxinin (20)

A Non-selective Rat GABAA Ion Channel [3H] TBOB Binding (Antagonist Radioligand) Assay (Catalog #3817) was conducted by Eurofins Pharma Discovery Service of Eurofins Cerep, France. The assay is based on these publications: Lewin, A. H. et al. Mol. Pharmacol. 1989, 35, 189, and Schwartz, R. D.; Mindlin, M. C. J. Pharmacol. Exp. Ther. 1987, 244, 963.

Compound binding was calculated as a percentage inhibition of the binding of the radioactive ligand [3H] TBOB (t-[3H]Butylbicycloorthobenzoate) for RAT GABAA Ion Channels.

A 20.0 mM stock solution was prepared in DMSO from pure solid 5-methyl-picrotoxinin (20) to evaluate radioligand displacement of [3H] TBOB from rat cerebral cortex GABA$_A$ receptors at final concentrations of 200 μM, 63 μM, 20 μM, 6.3 μM, 2.0 μM, and 0.6 μM. An IC50 value of 9.2 μM and a Ki value of 8.2 μM were determined for compound 20. Picrotoxinin (1) was used as a standard reference in this assay and exhibited an IC$_{50}$ value of 0.2 μM and a Ki value of 0.2 μM.

Numbered citations in the present disclosure are as follows:
1. Corey, E. J.; Pearce, H. L. Total synthesis of picrotoxinin. J. Am. Chem. Soc. 1979, 101, 5841.
2. Corey, E. J.; Pearce, H. L. Total synthesis of picrotin. Tetrahedron Lett. 1980, 21, 1823.
3. Niwa, H.; Wakamatsu, K.; Hida, T.; Niiyama, K.; Kigoshi, H.; Yamada, M.; Nagase, H.; Suzuki, M.; Yamada, K. Stereocontrolled total synthesis of (−)-picrotoxinin and (+)-coriamyrtin via a common isotwistane intermediate. *J Am. Chem. Soc.* 1984, 106, 4547.
4. Miyashita, M.; Suzuki, T.; Yoshikoshi, A., Stereoselective total synthesis of (−)-picrotoxinin and (−)-picrotin. *J. Am. Chem. Soc.* 1989, 111, 3728.
5. Trost, B. M.; Krische, M. J., A general strategy for the asymmetric synthesis of the picrotoxanes. *J. Am. Chem. Soc.* 1996, 118, 233.
6. Trost, B. M.; Haffner, C. D.; Jebaratnam, D. J.; Krische, M. J.; Thomas, A. P. The palladium-catalyzed enyne cycloisometization reaction in a general approach to the asymmetric syntheses of the picrotoxane sesquiterpenes. Part I. First-generation total synthesis of corianin and formal syntheses of picrotoxinin and picrotin. *J. Am. Chem. Soc.* 1999, 121, 6183.
7. Trost, B.; Krische, M. J. Palladium-catalyzed enyne cycloisomerization reaction in an asymmetric approach to the picrotoxane sesquiterpenes. 2. Second-generation total syntheses of corianin, picrotoxinin, picrotin, and methyl picrotoxate, *J. Am. Chem. Soc.* 1999, 121, 6131.
8. For a very recent approach, see: Cao, J.; Thor, W.; Yang, S.; Zhang, M.; Bao, W.; Zhu, L.; Yang, W.; Cheng, Y.-K.; Lee, C.-S. Synthesis of the tricyclic picrotoxane motif by an oxidative cascade cyclization, *Org. Lett.* 2019, 21, 4896.
9. Porter, L. A. Picrotoxinin and related substances. *Chem. Rev.* 1967, 67, 441.
10. Coscia, C. J. Picrotoxin. *Cyclopentanoid Terpene Derivatives"* 1968, pp. 147-201.
11: Gössinger, E. Picrotoxanes. *Progress in the Chemistry of Organic Natural Products*, vol. 93, 2010, Springer.
12. Fernandez, F.; Morishita, W.; Zuniga, E.; Nguyen, J.; Blank, M.; Malenka, R. C.; Garner, C. C. Pharmacotherapy for cognitive impairment in a mouse model of Down syndrome, *Nat. Neurosci.* 2007, 10, 411.
13. Picrotoxin; MSDS No. sc-202765 [Online]; Santa Cruz Biotechnology, Inc.: Santa Cruz, Calif., Dec. 23, 2008 http://datasheets.scbt.com/sc-202765.pdf (accessed Aug. 5, 2019),
14. Baker, M.; Demoret, R.; Ohtawa, M.; Shenvi, R. A. Concise asymmetric synthesis of (−)-bilobalide. *Nature,* 2019, 575, 643,
15. Witkin, J. M.; Shenvi, R. A.; Li, X.; Gleason, S. D.; Weiss, J.; Wakulchik, M. L.; Ohtawa, M.; Martinez, M. D.; Schkeryantz, J. M.; Carpenter, T. S.; Lightstone, F. C.; Ceme, R. Pharmacological characterization of the neurotrophic sesquiterpene jiadifenolide reveals a non-convulsant signature and potential for progression in neurodegenerative disease studies. *Biochem. Pham.* 2018, 155, 61.
16. Lu, H.-H.; Martinez, M. D.; Shenvi, R. A. An eight-step gram-scale synthesis of (−)-jiadifenolide. *Nature Chem.* 2015, 7, 604.
17. Ohtawa, M.; Krambis, M. J.; Cerne, R.; Schkeryantz, J.; Witkin, J. M.; Shenvi, R. A. Synthesis of (−)-11-O-debenzoyltashironin: Neurotrophic sesquiterpenes cause hyperexcitation. *J. Am. Chem. Soc.* 2017, 0.39, 9637.
18. Ng, C. C.; Duke, R. K.; Hinton, T.; Johnston, G. A. R. Effects of ginkgolide B and picrotoxinin on $GABA_A$ receptor modulation by structurally diverse positive modulators. *Eur. J. Pharm.* 2017, 806, 83.
19. For the generation of analogs from isolated picrotoxinin, see: a) Kriscshe, M. J.; Trost, B. M. Transformations of the picrotoxanes: the synthesis of corianin and structural analogs from picrotoxinin. *Tetrahedron* 1998, 54, 7109; b) Jarboe, C. H.; Porter, L. A.; Buckler, R. T. Structural Aspects of Picrotoxinin Action. *J. Med. Chem.* 1968, 11, 729; c) Shirai, Y.; Hosie, A. M.; Buckingham, S. D.; Holyoke, C. W.; Baylis, H. A.; Sattelle, D. B. Actions of picrotoxinin analogues on an expressed, homo-oligomeric GABA receptor of *Drosophila melanogaster. Neurosci. Lett,* 1995, 189,
20. Edwards, O. E.; Douglas, J. L.; Mootoo, B. Biosynthesis of dendrobine. *Can. J. Chem.* 1970, 48, 2517.
21. Maimone, T. J.; Baran, P. S. Modern synthetic efforts toward biologically active terpenes. *Nature Chem. Biol.* 2007, 3, 396.
22. Brill, Z. G.; Condakes, M. L.; Ting, C. P.; Maimone, T. J. Navigating the chiral pool in the total synthesis of complex terpene natural products. *Chem. Rev* 2017, 117, 11753.
23. Demoret, R. M.; Baker, M. A.; Ohtawa, M.; Chen, S.; Lam, C.-C.; Forli, S.; Houk, K.; Shenvi, R. A. Synthesis and Mechanistic Interrogation of *Ginkgo biloba* Chemical Space en route to (−)-Bilobalide; *ChemRxiv* DOI: 10.26434/chemrxiv.12132939.v2.
24. Smith, J. M.; Harwood, S. J.; Baran, P. S. Radical retrosynthesis. *Acc. Chem. Res.* 2018, 51, 1807.
25. Selezneva, N. K.; Gimalova, F. A.; Valeev, R. F.; Miftakhov, M. S. Efficient synthesis of (1R,4S,6R)-4-isopropenyl-1,3,3-trimethyl-7-oxabicyclo[4.1.0]heptan-2-one. *Russ. J. Org. Chem.* 2011, 47, 173.
26. Srikrishna, A.; Reddy, T. J.; Kumar, P. P. Synthesis of taxanes—the carvone approach; a simple, efficient enantioselective synthesis of the functionalized A ring. *Chem. Commun.* 1996, 1369.
27. Fabrissin, S.; Fatutta, S.; Risaliti, A. Elimination reactions of cis- and trans-8a-hydroxy-2-thiadecalin 2,2-dioxide with thionyl chloride. Evidence for intermediacy of ion pairs. *JCS, Perkin Trans.* 1 1977, 1561; Margaros, I.; Vassilikogiannakis, G. Synthesis of (+)-Zerumin B Using a Regioselective Singlet Oxygen Furan Oxidation. *J. Org. Chem.*, 2008, 73, 2021,
28. Dupau, P.; Epple, R.; Thomas, A. A.; Fokin, V. V.; Sharpless, K. B. Osmium catalyzed dihydroxylation of olefins in acidic media: Old process, new tricks. *Adv. Synth. Catal.* 2002, 344, 421.
29. [missing]
30. Dewick, P. M. (2009) *Medicinal Natural Products A Biosynthetic Approach,* 3rd ed., John Wiley & Sons, West Sussex, United Kingdom.
31. Nagel, R.; Peters, R. J. Diverging mechanisms: Cytochrome-P450-catalyzed demethylation and γ-lactone formation in bacterial gibberellin biosynthesis. *Angew. Chem. Int. Ed.* 2018, 57, 6082.
32. Roach, J. J.; Sasano, Y.; Schmid, C. L.; Zaidi, V. K.; Stevens, R. C.; Bohn, L. M.; Shensi, R. A. Dynamic strategic bond analysis yields a ten-step synthesis of 20-nor-salvinorin A, a potent κ-OR agonist. *ACS Cent. Sci.* 2017, 3, 1329.
33. a) Giri, R.; Yu, J.-Q. Iodine monoacetate. eEROS Encyclopedia of Reagents for Organic SynthesisDOI: 10.10021047084289X.m00915, 2008; b) Barnett, J. R.; Andrews, L. J.; Keefer, R. M. Trifluoroacetyl Hypohalites as Aromatic Halogenating Agents. *J. Am. Chem. Soc.* 1972, 94, 6129.
34. De Annas, P.; Francisco, C. G.; Suarez, E. Fragmentation of carbohydrate anomeric alkoxy radicals. tandem β-fragmentation-cyclization of alcohols. *J. Am. Chem. Soc.* 1993, 115, 8865.
35. a) Zombeck, A.; Hamilton, D. E.; Drago, R. S. Novel Catalytic Oxidations of Terminal Olefins by Cobalt(II)-Schiff Base Complexes. *J. Am. Chem. Soc.* 1982, 104, 6782; b) Mukaiyama, T.; Isayama, S.; Inoki, S.; Kato, K.; Yamada, T.; Takai, T. Oxidation-reduction hydration of olefins with molecular oxygen and 2-propanol catalyzed by bis(acetylacetonato)cobalt(II). *Chem. Lett* 1989, 449; c) Isayama, S.; Mukaiyama, T. A new method for preparation of alcohols from olefins with molecular oxygen and phenylsilane by the use of bis(acetylacetonato)cobalt(II). *Chem. Lett.* 1989, 1071.

36. Böttcher, T. An Additive Definition of Molecular Complexity. *J. Chem. Inf. Model.* 2016, 56, 462.

We claim:

1. The compound 5MePXN (20):

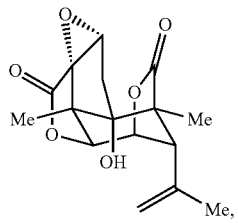

(20)

or a pharmaceutically acceptable salt thereof.

2. A pharmaceutical composition comprising the compound or pharmaceutically acceptable salt thereof according to claim 1 and a pharmaceutically acceptable carrier.

3. A method for antagonizing $GABA_A$ receptor, comprising contacting the receptor with an effective amount of the compound (20) or a pharmaceutically acceptable salt thereof according to claim 1.

4. The method according to claim 3, wherein the contacting occurs in vitro.

5. The method according to claim 3, wherein the contacting occurs in vivo.

6. A process for making the compound 5MePXN (20):

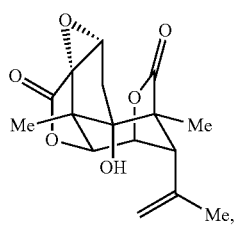

(20)

wherein the process comprises the steps of:

(b1) subjecting compound (8) to oxidation:

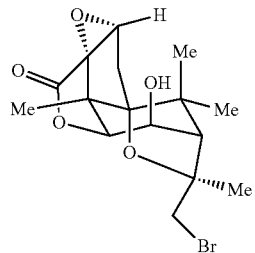

(8)

whereby compound (18) is formed:

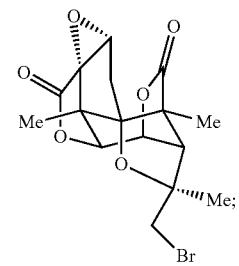

(18)

and (b2) subjecting compound (18) to reductive de-bromination whereby compound (20) is formed.

7. The process according to claim 6, wherein:

in step (b1), the oxidation comprises contacting compound (8) with iodine monoacetate; and/or in step (b2), the reductive de-bromination comprises contacting compound (18) with zinc(0)/$NH_4Cl$.

* * * * *